(12) United States Patent
Cetinkaya

(10) Patent No.: US 11,850,096 B1
(45) Date of Patent: Dec. 26, 2023

(54) METHOD AND APPARATUS FOR ULTRASONIC DELIVERY OF DRUGS AND CONTRAST AGENTS

(75) Inventor: Cetin Cetinkaya, Potsdam, NY (US)

(73) Assignee: Clarkson University

( * ) Notice: Subject to any disclaimer, the term of this patent is extended or adjusted under 35 U.S.C. 154(b) by 0 days.

(21) Appl. No.: 13/037,996

(22) Filed: Mar. 1, 2011

Related U.S. Application Data

(60) Provisional application No. 61/282,552, filed on Mar. 1, 2010.

(51) Int. Cl.
*A61B 8/08* (2006.01)
*A61K 49/22* (2006.01)
(Continued)

(52) U.S. Cl.
CPC ............... *A61B 8/481* (2013.01); *A61B 8/52* (2013.01); *A61B 8/5223* (2013.01);
(Continued)

(58) Field of Classification Search
USPC ................. 600/300, 407, 437, 458
See application file for complete search history.

(56) References Cited

U.S. PATENT DOCUMENTS

2005/0240126 A1* 10/2005 Foley ............... A61B 8/06 601/2
2005/0260189 A1* 11/2005 Klibanov et al. .......... 424/130.1
(Continued)

OTHER PUBLICATIONS

May 2002 Non-Lethal Swimmer Neutralization Study Applied Research Laboratories the University of Texas at Austin.*
(Continued)

*Primary Examiner* — Christopher Koharski
*Assistant Examiner* — Michael S Kellogg
(74) *Attorney, Agent, or Firm* — George McGuire

(57) ABSTRACT

A method, device and system for ultrasonic delivery and attachment of ligand-receptor based drugs and/or drug carriers and/or image enhancing contrast agents utilizing catch and slip bond mechanisms in a targeted part(s) of the human or animal (patient) body or organs or tissue is described and disclosed. The system includes an acoustic power source coupled to an acoustic transducer with the acoustic transducer placed upon a patient's delivery zone. The acoustic transducer transmits an acoustic field to the target drug delivery and/or imaging zone. A detection probe and/or a probe of an imaging system are placed over or within said delivery zone and the probe is coupled to a sensing/imaging system. A control computer that controls power and wave shape of the acoustic signal generated into the acoustic filed by the acoustic power source and receives data from the sensing/imaging system. This system utilizes catch and slip bonds for the delivery of drugs and/or drug carriers and/or image enhancing contrast agents. Placing an acoustic transducer over a delivery zone having ligand-receptor based drugs and/or drug carriers and/or image enhancing contrast agents. The method includes coupling an acoustic power source to said acoustic power source and installing a probe within or over said delivery zone. The probe is coupled to a sensing/imaging system. A control computer is used to control a power and a wave shape of the acoustic field generated by said acoustic transducer. The method uses a catch and slip bonds within said acoustic field to deliver ligand-receptor based drugs and/or drug carriers and/or image enhancing contrast.

6 Claims, 3 Drawing Sheets

(51) Int. Cl.
  *A61K 38/17* (2006.01)
  *A61K 47/69* (2017.01)
  *A61N 7/00* (2006.01)
(52) U.S. Cl.
  CPC .......... *A61B 8/5292* (2013.01); *A61K 38/177* (2013.01); *A61K 38/178* (2013.01); *A61K 47/6925* (2017.08); *A61K 49/22* (2013.01); *A61K 49/221* (2013.01); *A61K 49/222* (2013.01); *A61K 49/223* (2013.01); *A61K 49/227* (2013.01); *A61N 2007/0004* (2013.01); *A61N 2007/0039* (2013.01)

(56) References Cited

U.S. PATENT DOCUMENTS

| | | | |
|---|---|---|---|
| 2007/0197911 A1* | 8/2007 | Kaiser et al. | 600/437 |
| 2008/0319375 A1* | 12/2008 | Hardy | 604/22 |
| 2014/0142468 A1* | 5/2014 | Hossack et al. | 601/2 |

OTHER PUBLICATIONS

Enhanced Targeting of Ultrasound Contrast Agents Using Acoustic Radiation Force by Rychak et al. pub. Ultrasound in Med. & Biol., vol. 33, No. x, pp. xxx, 2007.*
Direct observation of catch bonds involving cell-adhesion molecules by Marshall et al. pub. Nature | vol. 423 | May 8, 2003.*
Bone Quantitative Ultrasound, CH2 pages, by Pascal Laugier and Guillaume Haïat, Publisher: Springer; 2011 edition (Dec. 1, 2010).*
Wave Propagation, <https://www.nde-ed.org/EducationResources/CommunityCollege/Ultrasonics/Physics/wavepropagation.htm> pub. online on Mar. 20, 2003 by the Nondestructuve Testing Resource Center.*
Acoustic Radiation Force Enhances Targeted Delivery of Ultrasound Contrast Microbubbles: In Vitro Verification by Rychak et al. pub. ieee transactions on ultrasonics, ferroelectrics, and frequency control, vol. 52, No. 3, Mar. 2005.*
Primary Bjerknes forces by T G Leighton et al. pub. 1990 Eur. J. Phys. issue 11 pp. 47-50.*
The Two-Pathway Model for the Catch-Slip Transition in Biological Adhesion by Pereverzev et al.; pub. Biophysical Journal vol. 89 Sep. 2005 1446-1454 (Year: 2005).*
Binding and detachment dynamics of microbubbles targeted to P-selectin under controlled shear flow by Takalkar et al.; pub. Journal of Controlled Release 96 (2004) 473-482 (Year: 2004).*
G.I. Bell, Models for the specific adhesion of cells to cells, Science 200 (1978), pp. 618-627.
M. Dembo, D.C. Torney, K. Saxman and D. Hammer, The reaction-limited kinetics of membrane-to-surface adhesion and detachmeot, Proc. R. Soc. Lond. B. Biol. Sci. 234 (1988), pp. 55-83.
W. E. Thomas, E. Trintchina, M. Forero, V. Vogel and E.V. Sokurenko, Bacterial adhesion to target cells enhanced by shear force, Cell 109 (2002), pp. 913-923.
B.T. Marshall, M. Long, J.W. Piper, T. Yago, R.P. McEver and C. Zhu, Direct observation of catch bonds involving cell-adhesion molecules, Nature 423 (2003), pp. 190-193.
P. Robert, A Benoliel, A. Pierres, and P. Bondrand, What is the biological relevance of the specific bond properties revealed by single molecule studies?, J. of Molecular Recognition, 20, pp. 432-447,2007.
P.F. Davies, Flow-mediated endothelial mechanotransduction, Physiol. Rev. 75 (1995), pp. 519-560.
Z. Guo, M. Moreau, D.W. Rickey, P.A. Picot and A. Fenster, Quantitative investigation of in vitro flow using three-dimensional colour Doppler ultrasound, Ultrasound Med. Biol. 21 (1995), pp. 807-816.
V. Vogel and M. Sheetz, Local force and geometry sensing regulate cell functions, Nat. Rev. Mol. Cell Biol. 7 (2006), pp. 265-275.
F., Evans and K. Ritchie, Dynamic strength of molecular adhesion bonds, Biophys. J. 72 (1997), pp. 1541-1555.
Evgeni V. Sokurenko, Viola Vogel and Wendy E. Thomas, Catch-Bond Mechanism of Force-Enhanced Adhesion: Counterintuitive, Elusive, but . . . Widespread?, Cell Host and Microbe, vol. 4, Issue 4,Oct. 16, 2008, pp. 314-323.
E.B. Finger, K.D. Puri, R. Alon, M.B. Lawrence, U.H. von Andrian and T.A. Springer, Adhesion through L-selectin requires a threshold hydrodynamic shear, Nature 379 (1996), pp. 266-269.
B. Savage, E. Saldivar and Z.M. Ruggeri, Initiation of platelet adhesion by arrest onto fibrinogen or translocation on von Willebrand factor, Cell 84 (1996), pp. 289-297.
K.C. Chang and D.A. Hammer, The forward rate of binding of surface-tethered reactants: effect of relative motion between two surfaces, Biophys. J. 76 (1999), pp. 1280-1292.
S. Chen and T.A. Springer, An automatic braking system that stabilizes leukocyte rolling by an increase in selectin bond number with shear, J. Cell Biol. 144 (1999), pp. 185-200.
S. Lu, Z. Ye, C. Zhu and M. Long, "Quantifying effects of contact duration, loading rate, and approach velocity on P-selectin-PSG1.-I interactions using AFM," Polymer 47, 2539 (2006).
Y. Pereverzev, O.V. Prezhdo, M. Forero, E. Sokurenko and W. Thomas, The Two-Pathway Model for the Catch-Slip Transition in Biological Adhesion, Biophys. J. 89 (2005), pp. 14461454.
Y.V. Pereverzev, O.V. Prezhdo, W.E. Thomas and E.V. Sokurenko, Distinctive features of the biological catch bond in the jump-ramp force regime predicted by the two-pathway model, Phys. Rev. E Stat. Nonlin. Soft Matter Phys. 72 (2005), p. 010903.
Y. Pereverzev and 0. Prezhdo, Force-Induced Deformations and Stability of Biological Bonds, Phys. Rev. E Stat. Nonlin. Soft Matter Phys. 73 (2006), p. 050902.
J. Lou, T. Yago, A.G. Klopocki, P. Mehta, W. Chen, V.I. Zarnitsyna, N.V. Bovin, C. Zhu and R.P. McEver, Flow-enhanced adhesion regulated by a selectin interdomain hinge, J. Cell Biol. 1'74 (2006), pp. 1107-1117.
B.H. Luo, K. Strokovich, T. Walz, T.A. Springer and J. Takagi, Allosteric beta1 integrin anti-bodies that stabilize the low affinity state by preventing the swing-out of the hybrid domain, J. Biol. Chem. 279 (2004), pp. 27466-27471.
W.E. Thomas, M. Forero, 0. Yakovenko, L. Nilsson, P. Viciai, E. Sokurenko and V. Vogel, Catch-bond model derived from allostery explains force-activated bacterial adhesion, Biophys. J. 90 (2006), pp. 753-764.
0. Yakovenko, S. Sharma, M. Forero, V. Tchesnokova, P. Aprikian, B. Kidd, A. Mach, V. Vogel, E. Sokurenko and W. Thomas, FimH forms catch bonds that are enhanced by mechanical force due to allosteric regulation, J. Biol. Chem. 283 (2008), pp. 11596-11605.
V. Barsegov and D. Thirumalai, Dynamics of unbinding of cell adhesion molecules: transition from catch to slip bonds, Proc. Nall. Acad. Sci. USA 102 (2005), pp. 1835-1839.
F.. Evans, A. Leung, V. Heinrich and C. Zhu, Mechanical switching and coupling between two dissociation pathways in a P-selectin adhesion bond, Proc. Nall. Acad. Sci. USA 101 (2004), pp. 11281-11286.
William G. Pitt, Ghaleb A. Husseini, and Bryant J. Staples, Ultrasonic Drug Delivery—A General Review, Expert Opin Drug Deliv. Nov. 2004; I(1): 37-56.
Unger E, Porter T, Culp W. Labell R, Matsunaga To, Zutshi R. Therapeutic Applications of Lipid-Coated Microbubbles. Adv Drug Deliv Rev. 2004:56(9):1291-1314.
Stride E, Saffari N. The Potential for Thermal Damage Posed by Microbubble Ultrasound Contrast Agents. Ultrasonics. 2004;42(1-9):907-13.
Schutt EH, Klein DH, Mattrey Rm, Riess JG. Injectable Microbubbles as Contrast Agents for Diagnostic Ultrasound Imaging; The Key Role of Perfluorochemicals. Angewandte Chemie—International Edition. 2003;42(28):3218-3235.
Niidome T, Huang L. Gene Therapy Progress and Prospects: Nonviral Vectors. Gene Therapy. 2002;9(24):1647-1652.
Price R, Kaul S. Contrast Ultrasound Targeted Drug and Gene Delivery: An Update on a New Therapeutic Modality. J Cardiovasc Pharmacol Therapeut. 2002;7(3):171-180.
Lindner L, Eichhorn Me, Eibl H, et al. Novel Temperature-Sensitive Liposomes with Prolonged Circulation Time. Clinical Cancer Research. 2004;10(6):2168-2178.

(56) References Cited

OTHER PUBLICATIONS

Miller D, Pislaru Sv, Greenleaf J. Sonoporation: Mechanical DNA Delivery by Ultrasonic Cavitation. Somatic Cell Molec Genetics. 2002;27(1):115-134.
Shohet RV, Chen S, Zhou Y-T, et al. Echocardiographic Destruction of Albumin Microbubbles Directs Gene Delivery to the Myocardium. Circulation. 2000;101:2554-2556.
Lawrie A, Brisken AF, Francis Se, Cumberland Dc, Crossman Dc, Newman Cm. Microbubble-Enhanced Ultrasound for Vascular Gene Delivery, Gene Ther. 2000;7(23):20232027.
Miura S, Tachibana K, Okamoto T, Saku K. In Vitro Transfer of Antisense Oligodeoxynucleotides Into Coronary Endothelial Cells by Ultrasound. Biochem Biophys Res Commun. 2002;298(4):587-590.
37. Teupe C. Richter S, Fissithaler B, et al. Vascular Gene Transfer of Phosphomimetic Endothelial Nitric Oxide Synthase (S1177d) Using Ultrasound-Enhanced Destruction of Plasmid-Loaded Microbubbles Improves Vasoreactivity. Circulation. 2002:1104-1109.
Beeri R, Guerrero JI, Supple G, Sullivan S, Levine Ra, Hajjar Rj. New Efficient Catheter-Based System for Myocardial Gene Delivery, Circulation. 2002;106(14):1756-1759.39. Endoh M, Koibuchi N, Sato M, et al.
Endoh M. Koibuchi N, Sato M, et al. Fetal Gene Transfer by Intrauterine Injection with Microbubble-Enhanced Ultrasound. Molecular Therapy. 2002;5(5):501-508.
Unger Ec, Fritz Ta, Matsunaga T, Ramaswami Vr, Yellowhair D, Wu G: Therapeutic Drug Delivery Systems. In: U. S. Patent Database Imarx Pharmaceutical Corp; United States of America: (1996):48.
Unger EC, Mccreery TP, Sweitzer RH. Ultrasound Enhances Gene Expression of Liposomal Transfection. Investigative Radiology. 1997;32(12):723-727.
Lawrie A, Brisken AF, Francis Se, Et al. Ultrasound Enhances Reporter Gene Expression after Transfection of Vascular Cells In Vitro. Circulation. 1999:99(20):2617-2620.
Mccreery TP, Sweitzer RH, Unger EC: Dna Delivery to Cells in Culture Using Ultrasound. In: Methods in Molecular Biology vol. 245. Heiser Wc, Ed. Humana Press; Totowa, New Jersey: (2004):287-291.
Mccreery TP, Sweitzer RH, Unger EC: Dna Delivery to Cells In Vivo by Ultrasound. In: Methods in Molecular Biology vol. 245, Heiser Wc, Ed. Humana Press; Totowa, New Jersey: (2004):293-298.
Taniyama V, Tachibana K, Hiraoka K, et al. Local Delivery of Plasmid DNA into Rat Carotid Artery Using Ultrasound. Circulation. 2002;105(10):1233-1239.
Riesz P, Kondo T. Free-Radical Formation Induced by Ultrasound and Its Biological Implications. Free Radical Biology and Medicine. 1992;13(3):247-270.
Kuo JHS, Jan MS, Sung KC. Evaluation of the Stability of Polymer-Based Plasmid DNA Delivery Systems After Ultrasound Exposure. International Journal of Pharmaceutics, 2003;257(1-2):75-84.
Anwer K, Kao G, Proctor B, et al. Ultrasound Enhancement of Cationte Lipid-Mediated Gene Transfer to Primary Tumors Following Systemic Administration. Gene Therapy. 2000;7(21):1833-1839.
Lindner JR. Microbubbles in Medical Imaging: Current Applications and Future Directions. Nature Reviews Drug Discovery, 2004:3(6):527-532.
Amabile PG, Waugh JM, Lewis TN, Elkins CJ, Janas W, Dake MD, High-Efficiency Endovascular Gene Delivery via Therapeutic Ultrasound. Journal of the American College of Cardiology. 2001;37 (7):1975-1980.
Manome Y, Nakamura M, Ohno T, Furuhata H. Ultrasound Facilitates Transduction of Naked Plasmid DNA Into Colon Carcinoma Cells In Vitro and In Vivo. Human Gene Therapy. 2000;11(11):1521-1528.
Barbarese E, Ho S-Y, D'arrigo JS, Simon RH. Internalization of Microbubbles by Tumor Cells In Vivo and In Vitro, Journal of Neuro-Oncology. 1995;26;25-34.

Cho C-W, Liu Y, Cobb WN, et al. Ultrasound-Induced Mild Hyperthermia as a Novel Approach to Increase Drug Uptake in Brain Microvessel Endothelial Cells. Pharm Res. 2002;19(8):1123-1129.
Mesiwala Ah, Farrell L, Wenzel Hj, Et al. High-Intensity Focused Ultrasound Selectively Disrupts the Blood-Brain Barrier In Vivo. Ultrasound Med Biol. 2002:28(3):389-400.
Cho Cw, Liu Y, Cobb WN, Et al. Ultrasound-Induced Mild Hyperthermia as a Novel Approach to Iacrease Drug Uptake in Brain Microvessel Endothelial Cells. Pharmaceutical Research. 2002;19(8):1123-1129.
Hynynen K, Mcdannold N, Martin H, Jolesz Fa, Vykhodtseva N. The Threshold for Brain Damage in Rabbits Induced by Bursts of Ultrasound in the Presence of an Ultrasound Contrast Agent (Optison (R)), Ultrasound in Medicine and Biology. 2003; 29(3):473-481.
Guillaume C, Delepine P, Droal C, Montier T, Tymen G, Claude F. Aerosolization of Cationic Lipid—DNA Complexes: Lipoplex Characterization and Optimizatian of Aerosol Delivery Conditions. Biochem Biophys Res Commun. 2001;286(3):464-471.
Pillai R, Petrak K, Blezinger P, Et al., Ultrasonic Nehulizatian of Cationic Lipid-Based Gene Delivery Systems for Airway Administration. Pharm Res. 1998;15(11):1743-1747.
Mitragotri S, Kost J. Low-Frequency Sonophoresis. A Review. Adv Drug Deliv Rev. 2004;56:589-601.
Barry Bw, Novel Mechanisms and Devices to Enable Successful Transdermal Drug Delivery. European Journal of Pharmaceutical Sciences. 2001;14:101-114.
Prausnitz MR. Reversible Skin Permeabilization for Transdermal Delivery of Macromolecules. Critical Reviews in Therapeutic Drug Carrier Systems. 1997;14(4):455-483.
Guy RH, Current Status and Future Prospects of Transdermal Drug Delivery. Pharm Res. 1996; 13(12):1765-1769.
Kassan DG, Lynch Am, J Sm. Physical Enhancement of Dermatologic Drug Delivery Iontophoresis and Phonophoresis. J Amer Acad Dermatology. 1996;34(4):657-666.
Byl N. The Use of Ultrasound as an Enhancer for Transcutaneous Drug Delivery: Phonophoresis, Physical Therapy, 1995;75(6):539-553.
Tyle P, Agrawala P. Drug Delivery by Phonophoresis. Pharm Res. 1989;6(5):355-361.
Skauen Dm, Zentner GM. Phonophoresis. Int J Pharmaceutics. 1984;20:235-245.
Bommannan D, Okuyama Il, Stauffer P, Guy RH, Sooophoresis, 1 the Use of High-Frequency Ultrasound to Enhance Transdermal Drug Delivery. Pharm Res. 1992;9(4):559-564.
Bommannan D, Menon GK, Okuyama II, Elias PM, Guy RH, Sooophoresis, Ii Examination of the Mechanism(S) of Ultrasound-Enhanced Transdermal Drug Delivery, Pharm Res. 1992;9(8):1043-1047.
Menon GK, Bommannan DB, Elias PM. High-Frequency Sonophoresis: Permeation Pathways and Structural Basis for Enhanced Permeability, Skin Pharmacol. 1994;7:130-139.
Vyas Sp, Singh R, Asati Rk. Liposomally Encapsulated Diclofenac for Sonophoresis Induced Systemic Delivery. J Microencapsul. 1995;12(2):149-154.
Mitragotri S. Synergistic Effect of Enhancers for Transdermal Drug Delivery, Pharm Res. 2000:17(11):1354-1357.
Johnson ME, Mitragotri S, Patel A, Blankschtein D, Langer R. Synergistic Effects of Chemical Enhancers and Therapeutic Ultrasound on Transdermal Drug Delivery. Journal of Pharmaceutical Sciences. 1996;85(7):670-677.
Tezel A, Sens A, Tuchscherer J, Mitragotri A. Synergistic Effect of Low-Frequency Ultrasound and Surfactants on Skin Permeability. J Pharm Sci. 2002:91(1):91-100.
Wu J, Chappelow J, Yang J, Weimann L. Defects Generated in Human Stratum Corneum Specimens by Ultrasouod. Ultrasound in Med & Biol. 1998;24(5):705-710.
Yamashita N, Tachibana K, Ogawa K, Tsujita N, Tomita A. Scanning Electron Microscopic Evaluation of the Skin Surface After Ultrasound Exposure, Anatom Rec. 1997;247:455-461.
Tezel A, Mitragotri S. On the Origin of Size-Dependent Tortuosity for Permeation of Hydrophilic Solutes Across the Stratum Corneum. Journal of Controlled Release. 2003;86(t):t83-186.

(56) References Cited

OTHER PUBLICATIONS

Tezel A, Sens A, Mitragotri S. Description of Transdermal Transport of Hydrophilic Solutes During Low-Frequency Sonophoresis Based on a Modified Porous Pathway Model. 2003;92(2):381-393.

Kwok CS, Mourad PD, Crum LA, Ratner BD. Self-Assembled Molecular Structures as Ultrasonically-Responsive Barrier Membranes for Pulsatile Drug Delivery. J Biomed Mater Res. 2001;57:151-164.

Francis CW, Onundarson PT, Carstensen El, et al. Enhancement of Fibrinolysis In Vitro by Ultrasound. J Clin Invest. 1992;90(11):2063-2068.

Lauer CG, Burge R, Tang DB, Bass BG, Gomez Er, Alving Bm. Effect of Ultrasound on Tissue-Type Plasminogen Activator-Induced Thrombolysis. Circulation. 1992;86:1257-1264.

Wu YQ, Unger EC, Mccreery TP, et al. Binding and Lysing of Blood Clots Using Mrx-408, Investigative Radiology. 1998;33(12):880-885.

Culp WC, Porter TR, Lowery J, Roberson PK, Xie F, Mccowan TC. Intracranial Clot Lysis With Intravenous Platelet Targeted Microbubbles and Transcranial Ultrasound. Circulation. 2003;108(17):604-604.

Kost J. Ultrasound for Controlled Delivery of Therapeutics, Clinical Materials. 1993;13:155161.

Loverock P, Ter Haarg, Ormerod MG, Imrie PR. The Effect of Ultrasound on the Cytoxicity of Adriamycin. Brit J Radiol. 1990; 63:542-546.

McCulloch, M., C. Gresser, S. Moos, J. Odabashian, S. Jasper, J. Bednarz, P. Burgess, D. Carney, V. Moore, E. Sisk, A. Waggoner, S. Witt, and D. Adams. Ultrasound contrast physics: A series on contrast echocardiography. J Am Soc Echocardiogr. 13:10, pp. 959-967,2000.

Harisinghant, Mukesh G.; Weissleder, Ralph; Schima, Wolfgang; Saini, Sanjay; Hahn, Peter F.; Mueller, Peter R. (2001), MRI Contrast Agents for Evaluating Focal Hepatic Lesions, 56, Clinical Radiology, pp. 714-725).

Contrast Agents II: Optical, Ultrasound, X-Ray Imaging and Radiopharmaceutical Imaging (Topics in Current Chemistry, Werner Krause (Editor), 2010, Springer.

* cited by examiner

METHOD AND APPARATUS FOR ULTRASONIC DELIVERY OF DRUGS AND CONTRAST AGENTS

CROSS REFERENCE

This application is related to provisional application Ser. No. 61/282,552 filed on Mar. 1, 2010 entitled "Method, Device and System for Ultrasonic Delivery of Ligand-receptor Based Drugs Utilizing Catch and Slip Bonds" and is hereby incorporated herein by reference.

FIELD OF INVENTION

A method, device and system for ultrasonic delivery and attachment of ligand-receptor based drugs and/or drug carriers and/or image enhancing contrast agents utilizing catch and slip bond mechanisms in a targeted part(s) of the human or animal (patient) body or organs or tissue is described and disclosed.

BACKGROUND

Introduction

The approach herein is based on the experimental-observed fact that the strength and/or lifetime of certain classes of ligand-receptor bonds (e.g. catch and slip bonds) are enhanced or shortened/weakened by external stress, moment and/or strains on the bond or other parts of the molecules involved. Biological or man-made objects (e.g. drug carriers containing drug such as micro/nano-particles, microbubbles, liposomes, micelles, vesicles, and free genetic materials) with a receptor that can form a catch bond with its ligand(s) can be attached to surfaces containing these ligand(s) in a specific range of external forces and moments creating a strain (stress) level in the bond or other parts of the molecules involved. Below the lower bound and above the upper of this range in a catch bond the bonding is unlikely and/or with very short lifetimes. In many cases, the external stress/moment/strain on the bond is exerted by a shear field generated by fluid flow, such as blood circulation. Slip bonds, weakened as a result of an external mechanical effect, are utilized to detach biological objects. In disclosure below is described the required external stress/moment/strain with ultrasonically applied signals to a delivery or imaging zone in the patient's body or organ or tissue that is targeted for drug therapy and/or medical imaging as the drug loaded objects (i.e. drug carriers) and/or imaging contrast agents with engineered receptors or ligands are circulated in the blood or interstitial fluids, and/or diffuse in tissue. The acoustic external pressure field changes the configuration of the molecules leading to desired bonding effect in a specific zone where delivery and/or imaging is required. These objects upon attachment which are controlled by a ligand-receptor bond (e.g. catch bond) begin delivering drug either automatically and/or by an external source (such another ultrasonic field, chemical enhancer, electromagnetic effects, thermal effect, etc.). In the case of medical imaging, carriers contain contrast agents to enhance imaging quality (such as resolution, contrast, etc.) in the zone of interest. Their detachment (if need be) can be realized by activating ligand-receptor bonds (e.g. slip bonds) by an ultrasonic field with a set of certain characteristics (e.g. frequency contents, amplitude (power), duty cycle, focusing parameters, etc.). Similarly, two or more circulated objects in the circulation system and/or diffusing in tissue can also be activated to bond or de-bond in a non-contact manner in a controllable fashion in the delivery zone. These bonded composite drugs and drug carrier objects and/or imaging contrast (e.g. large molecules, large molecule coated particles, bubbles, liposomes, micelles, vesicles, etc.) can also be attached (or detached) to the target drug delivery or imaging zone using the same mechanism, or automatically attaches (detaches) to (from) their target zones. A possible embodiment of the design is described, and various other embodiments are detailed and discussed.

Background: Observations about Catch and Slip Ligand-Receptor Bonds

Living organisms consist mostly of water-based fluids, and, due to boundary layer formation, their flow along a surface creates a shear stress field and rolling moment for objects attached to a surface (FIG. 1.A). Resistance to detachment by shear stress is considered a critical characteristic of biological adhesion, since most adhesive interactions between bacterial/eukaryotic cells and surfaces are initiated and must be sustained under flow conditions. For example, shear stress is created by flow from the heart pumping blood, saliva secretion, and emptying of the urinary bladder. Vascular endothelial cells arm exposed to fluid shear stresses that are typically 0.1-0.2 Pa on the venous side and 1-2 Pa (up to 5.0 Pa) on the arterial side of the circulation. (See P. F. Davies, Flow-mediated endothelial mechanotransduction. *Physiol. Rev.* 75 (1995), pp. 519-560 and Z. Guo, Moreau, D. W. Rickey, P. A. Picot and A. Fenster, Quantitative investigation of in vitro flow using three-dimensional color Doppler ultrasound, *Ultrasound Med. Biol.* 21 (1995), pp. 807-816.

During adhesion ligand-receptor bonds must accommodate the need for sustained attachment and simultaneously allow for cell migration or spreading on surfaces. These processes involve the continuous formation and breakage of cell-surface bonds or intercellular interactions. (See V. Vogel and M. Sheetz, Local force and geometry sensing regulate cell functions. *Nat Rev. Mal. Cell Biol.* 7 (2006), pp. 265-275.) An important subset of these bonds are catch bonds, which are ligand-receptor bonds that are enhanced by mechanical (translational) force pulling the ligand-receptor pair apart (FIG. 1.C), unlike slip bonds (FIG. 1.B). To date, catch-bond formation has been reported for *E. coli* adhesion, myosin from actin, FimH, and for P-/L-selectins which are expressed by leukocytes, platelets, and blood vessel walls. Catch bonds must be distinguished from slip bonds, (See M. Dembo, D. C. Tomey, K. Saxman and D. Hammer, The reaction-limited kinetics of membrane-to-surface adhesion and detachment, *Proc. R. Soc. Land. Biol. Sci.* 234 (1988), pp. 55-83.) which are more intuitive, where the probability of bond rupture increases when ligand-receptor pairs are subjected to an increasing tensile force (FIG. 1.B). (See G. I. Bell, Models for the specific adhesion of cells to cells, *Science* 200 (1978), pp. 618-627; M. Dembo, D. C. Tomey, K. Saxman and D. Hammer, The reaction-limited kinetics of membrane-to-surface adhesion and detachment, *Proc. R. Soc. Land. Biol. Sci.* 234 (1988), pp. 55-83; and F. Evans and K. Ritchie, Dynamic strength of molecular adhesion bonds, *Biophys. J.* 72 (1997), pp. 1541-1555.)

FIG. 1 (A) illustrates a schematic presentation of drag (shear) force on an adhering cell. FIG. 1 (B) illustrates the dependence of the lifetime of receptor-ligand interactions on the force level in slip bonds. FIG. 1 (C) illustrates the dependence of the lifetime of receptor-ligand interactions on the force level in catch bonds. Note that the full-in ligand configuration corresponds to strong binding (low probability of the bond dissociation), while half-in ligand or open receptor configurations correspond to weak binding (high probability of the bond dissociation). FIG. 2 illustrates experimental evidence for catch bonds. In particular FIG. 2 (A) illustrates the rolling velocity of red blood cells over a carpet of type 1-fimbriated *E. coli*, dependent on shear level). FIG. 2(B) illustrates the accumulation of type 1 fimbriated *E. coli* on a mannosylated surface, dependent on shear level. FIG. 2(C) the lifetime of P-selectin-PSGL-1 bonds, dependent on the level of tensile force applied by AFM (red: FimH; hint: V156P FimH mutant). (FIGS. 1 and 2 were originally published by Evgeni V. Sokurenko, Viola Vogel and Wendy E. Thomas, Catch-Bond Mechanism of Force-Enhanced Adhesion: Counterintuitive, Elusive, but . . . Widespread?, Cell Host and Microbe, Volume 4, Issue 4, 16 Oct. 2008, Pages 314-323.)

Most studies of catch bond formation have been motivated by the desire to understand leukocyte (white blood cells) rolling, which is commonly observed during inflammation, and is mediated by a series of ligand-receptor interactions between the cell surface and tissue surface. The most important ligand-receptor interaction has been identified as that between P-selectin, a cell adhesion molecule on the surfaces of activated endothelial cells, which line the inner surface of blood vessels, and P-selectin glycoprotein ligand-1 (PSGL-1), a glycoprotein found on white blood cells and endothelial cells. Indeed, despite the existence of many different proteins on cell surfaces, numerous studies have reported that repeated bond formation and dissociation solely involving P-selectin and PSGL-1 in various model systems can result in cell rolling. (See E. B. Finger, K. D. Puri, R. Alon, M. B. Lawrence, U. H. von Andrian and T. A. Springer, Adhesion through L-selectin requires a threshold hydrodynamic shear, *Nature* 379 (1996), pp. 266-269.)

The level of (applied) shear stress is critical to this process, since it is now clear that without shear, leukocytes do not bind to an endothelial or PSGL-1 coated surface, but that above a certain shear threshold, they are able to attach in a rolling fashion. (See E. B. Finger, K. D. Puri, R. Alon, M. B. Lawrence, U. H. von Andrian and T. A. Springer, Adhesion through L-selectin requires a threshold hydrodynamic shear, *Nature* 379 (1996), pp. 266-269. If the flow speed is reduced, the rolling cells completely detach from the surface. These phenomena were explained by first the postulation, (See M. Dembo, D. C. Tomey, K. Saxman and D. Hammer. The reaction-limited kinetics of membrane-to-surface adhesion and detachment, *Proc. R. Soc. Land B. Biol. Sci.* 234 (1988), pp. 55-83.) and then the observation (See W. E. Thomas, F. Trintchina, M. Forero, V. Vogel and E. V. Sokurenko, Bacterial adhesion to target cells enhanced by shear force, *Cell* 109 (2002), pp. 913-923.), of catch bond formation. Leukocyte rolling is quite complex, as described in a recent review article, (See P. Robert, A Benoliel, A. Pierres, and P. Bondrand, *What is the biological relevance of the specific bond properties revealed by single molecule studies?*, J. of Molecular Recognition, 20, pp. 432-447, 2007.) and detailed mechanistic understanding can only be obtained through quantitative understanding of a wide variety of physical chemical phenomena, including the wall shear stress; cell radius and cell density; microvillus length, radius, and density; PSGL-1 size and density; P-selectin size and density; the length, formation rate, dissociation rate, and spring constant of the bond between PSGL-1 and P-selectin; and environmental factors such as temperature, fluid density, and fluid viscosity. (See P. Robert, A Benoliel, A. Pierres, and P. Bondrand, *What is the biological relevance of the specific bond properties revealed by singe molecule studies?*, J. of Molecular Recognition, 20, pp. 432-447, 2007.)

As described further below, accurate measurements of many of these quantities is quite challenging. Accurate measurements require the use of tightly controlled receptor concentrations on well-characterized surfaces. Despite the conceptual inception of the catch bond model in 1988, no experimental study prior to 2002 had been reported for shear-enhanced adhesion. (See W. E. Thomas, E. Trintchina, M. Forero, V. Vogel and E. V. Sokurenko, Bacterial adhesion to target cells enhanced by shear force, *Cell* 109 (2002), pp. 913-923.)

The first experimental work (See W. E. Thomas, E. Trintchina, M. Forero, V. Vogel and E. V. Sokurenko, Bacterial adhesion to target cells enhanced by shear force, *Cell* 109 (2002), pp. 913-923.) that claimed to identify a force-enhanced receptor-ligand interaction utilized *E. coli* that possess type 1 fimbriae (also referred to as pili). These hair-like surface appendages present on their tip a mannose-binding adhesion, the 30 kDa protein FimH. In this study fimbriated bacteria were immobilized on the surface of a flow chamber. Then, guinea pig red blood cells (rich in mannosylated glycoproteins) (a diameter of 6-8 μm) were loaded on the bacterial carpet; the washing buffer was flowed at different rates and the behavior of the erythrocytes on the surface was monitored by video microscopy. When the buffer flow was slow (creating shear stress of 0.02 dynes/cm$^2$) red blood cells that were attached to the bacterial carpet moved along the surface (FIG. 2). As the washing buffer was fed into the flow chamber at an increased velocity, the rolling velocity at first increased, but then suddenly dropped, with all red blood cells becoming stationary at a shear range of −0.15-0.8 dynes/cm$^2$. Thus, it is concluded that the binding strength between red blood cells and the mannose-specific fimbriae of *E. coli* was enhanced by shear. Unlike the previous studies that reported shear-enhanced adhesion, special attempts were made in this study examined the structural origin of the observation. The main question was whether it was dependent on the effect of tensile force on the intrinsic properties of individual bonds. It was proposed that shear-enhanced FimH-mediated adhesion depends on a conformational change in FimH that, according to SMD, occurred under tensile force after the mannose binding, thus affecting (decreasing) the bonds off rates. This conclusion was in contrast to prior studies on shear-enhanced cell adhesion that suggested that the phenomenon was caused by increased on rates of the bonds. (See B. Savage, E. Saldivar and Z. M. Ruggeri, Initiation of platelet adhesion by arrest onto fibrinogen or translocation on von Willebrand factor, *Cell* 84 (1996), pp. 284-297; K. C. Chang and D. A. Hammer. The forward rate of binding of surface-tethered reactants: effect of relative motion between two surfaces, *Biophys. J.* 76 (1999), pp. 1280-1292; and S. Chen and T. A. Springer, An automatic braking system that stabilizes leukocyte rolling by an increase in selectin bond number with shear, *J. Cell Biol.* 144 (1999), pp. 185-200.)

Atomic force microscopy (AFM) was used to stretch a bond between P-selectin and PSGL-1 (its ligand). (See B. T. Marshall, M. Long, J. W, Piper, T. Yago, R. P. McEver and C. Zhu, Direct observation of catch bonds involving cell-adhesion molecules, *Nature* 423 (2003), pp. 190-193.) The response of individual receptor-ligand interactions to tensile force could be measured. P-selectin is a receptor protein expressed by activated endothelial cells that recognize PSGL-1 expressed on the surface of leukocytes. Leukocyte binding to the endothelium requires a certain shear threshold. This surface rolling allows cells to slow down in rapidly flowing blood enough to interact with other signals in the vessel wall and is involved in immune responses, inflammation, homeostasis, and thrombosis. An AFM cantilever was coated with PSGL-1 and is used to probe a supported lipid bilayer containing P-selectin. Upon formation of a single P-selectin-PSGL-1 bond, the cantilever was pulled away to create a certain level of constant force on the bond. The time it took for the bond to break (dissociate) under a defined force level was recorded. The lifetime of bonds steadily increased with an incremental rise in the level of force from 5 pN to 11 pN (FIG. 2C). A further increase in tensile force resulted in the increase of dissociation rate as the bonds were subjected to excessive force. The increase in bond strength with a moderate force could not be explained by a slip-bond mechanism of the interaction. One of the most direct methods to observe and quantify catch bond formation is to immobilize one of these molecules onto an extended surface, and the other onto the cantilever tip of an AFM. (See B. T. Marshall, M. Long, J. W. Piper, T. Yago, R. P. McEver and C. Zhu, Direct observation of catch bonds involving cell-adhesion molecules. *Nature* 423 (2003), pp. 190-193; and S. Lu, Z. Ye, C. Zhu and M. Long, "Quantifying effects of contact duration, loading rate, and approach velocity on P-selectin-PSGL-1 interactions using AFM," *Polymer* 47, 2539 (2006).)

Current Models for the Catch Bond Mechanism:

Most of the predictions fir how catch bonds work have been made by fitting the kinetics of adsorption and unbinding with mathematical models. Four major models have been advanced in recent years: (i) The two-pathway model is where the ligand can exit from the binding pocket of the receptor via two different ways (pathways with different energy barrier heights)—one relatively easy and another not as easy—and where a sufficiently strong force only allows the ligand to escape via the difficult pathway. (See Y, Pereverzev, O. V. Prezhdo, M. Forero, E. Sokurenko and W. Thomas. The Two-Pathway Model for the Catch-Slip Transition in Biological Adhesion, *Biophys. J.* 89 (2005), pp. 1446-1454 and Y. V. Pereverzev, O. V, Prezhdo, W. E. Thomas and E. V. Sokurenko, Distinctive features of the biological catch bond in the jump-ramp force regime predicted by the two-pathway model, *Phys. Rev. F Stat. Nonlin. Soft Matter Phys.* 72 (2005), p. 010903.) This mechanism can be similar to two hooks locked together and which can easily separate if they are not being pulled against each other, but catch one another stably when tensile force is applied; (ii) The deformation model is where tensile force directly causes a conformational change of the binding pocket and/or ligand, resulting in a tighter fit. (See Y. Pereverzev and O. V. Prezhdo, Force-Induced Deformations and Stability of Biological Bonds. *Phys. Rev. E Stat. Nonlin. Soft Matter Phys.* 73 (2006), p. 050902.) This model is somewhat analogous to the mechanism underlying the "finger-trap" toy—a short mesh tube that narrows and tightens when stretched by fingers inserted in each end, effectively gripping and entrapping them inside the tube; (iii) The sliding-rebinding model is where flexibility of the receptor protein under force leads to alignment of the ligand and binding pocket interface in parallel fashion, allowing new binding contacts to form and the original contacts to rebind (See J Lou, T. Yago, A. G. Klopocki, P. Mehta, W, Chen, V. I. Zarnitsyna, N. V. Bovin, C. Zhu and R. P. McEver, Flow-enhanced adhesion regulated by a selectin interdomain hinge, *J. Cell Biol.* 174 (2006), pp. 1107-1117 and B. H. Luo, K. Strokovich, T. Walz, T. A. Springer and J. Takagi, Allosteric beta1 integrin anti-bodies that stabilize the low affinity state by preventing the swing-out of the hybrid domain, *J. Biol. Chem.* 279 (2004), pp. 27466-27471.); (iv) The allosteric model is where force-induced structural alterations in one part of the receptor protein are linked to a shift from low- to high-affinity conformation of the ligand-binding site located in another part of the protein. (See W. E. Thomas, M. Forero, O. Yakovenko, L. Nilsson, P. Vicini, E. Sokurenko and V. Vogel, Catch-bond model derived from allostery explains force-activated bacterial adhesion, *Biophys. J.* 90 (2006), pp. 753-764 and O. Yakovenko, S. Sharma, M. Forero, V. Tchesnokova, P. Aprikian, B. Kidd, A. Mach. V. Vogel, E. Sokurenko and W. Thomas, FimH forms catch bonds that are enhanced by mechanical force due to allosteric regulation, *J. Biol. Chem.* 283 (2008), pp. 11596-11605.) The two-state model (See V. Barsegov and D. Thirumalai, Dynamics of unbinding of cell adhesion molecules: transition from catch to slip bonds, *Proc. Natl. Acad, Sci. USA* 102 (2005), pp. 1835-1839 and E. Evans, A. Leung, V. Heinrich and C. Zhu, Mechanical switching and coupling between two dissociation pathways in a P-selectin adhesion bond, *Proc. Natl. Acad Sci. USA* 101 (2004), pp. 11281-11286.) is mathematically similar in most respects to the allosteric one.

Review of Existing Techniques and Potential Drug Delivery and Imaging Applications Below various types of application areas of the disclosed embodiments have been reviewed and the current state of relevant targeted drug delivery technologies is discussed in detailed, based on the literature. (See William G. Pitt, Ghaleb A, Husseini, And Bryant J. Staples, Ultrasonic Drug Delivery—A General Review, Expert Opin Drug Deliv. 2004 November; 1(1): 37-56.)

DNA and Gene Delivery

Gene delivery is an important application area of targeted drug delivery. (Unger E, Porter T, Culp W, Labell R, Matsunaga To, Zutshi R. Therapeutic Applications of Lipid-Coated Microbubbles. Adv Drug Deliv Rev. 2004; 56(9): 1291-1314; Stride E, Saffari N. The Potential for Thermal Damage Posed by Microbubble Ultrasound Contrast Agents. Ultrasonics. 2004; 42(1-9):907-13; Schutt E H, Klein D H, Mattrey Rm, Riess J G. Injectable Microbubbles as Contrast Agents for Diagnostic Ultrasound Imaging: The Key Role of Perfluorochemicals. Angewandte Chemie-International Edition. 2003; 42(28):3218-3235; Niidome T, Huang L. Gene Therapy Progress And Prospects: Nonviral Vectors. Gene Therapy. 2002; 9(24):1647-1652; Price R, Kaul S. Contrast Ultrasound Targeted Drug and Gene Delivery: An Update on a New Therapeutic Modality. J Cardiovasc Pharmascol Therapeut. 2002; 7(3):171-180; Lindner L, Eichhorn Me, Eibl H, et al. Novel Temperature-Sensitive Liposomes with Prolonged Circulation Time. Clinical Cancer Research. 2004; 10(6):2168-2178; and Miller D, Pislaru Sv, Greenleaf J. Sonoporation: Mechanical DNA Delivery By Ultrasonic (Cavitation. Somatic Cell Molec Genetics. 2002; 27(1):115-134. The use of ultrasound in gene delivery has exceptional potential because the beam can bet focused on a particular tissue. The main issue is to release the genetic material only at the targeted site with minimal collateral damage. One possible complication comes from the fact that the DNA (or RNA) must enter the targeted cells before it is degraded by DNase or carried to other tissues by the blood.

Ultrasonically Activated Gene Carriers Microbubbles:

Gene delivery using microbubbles under ultrasound has been known since 2000. (See Shohet R V, Chen S, Zhou Y-T, et al. Echocardiographic Destruction of Albumin Microbubbles Directs Gene Delivery to The Myocardium. Circulation. 2000; 101:2554-2556 and Lawrie A, Brisken A F, Francis Se, Cumberland De, Crossman De, Newman Cm. Microbubble-Enhanced Ultrasound for Vascular Gene Delivery, Gene Ther. 2000; 7(23):2023-2027.) Since then has been a topic of intense study. The interest in this technique mainly arises from the availability of commercial ultrasound contrast agents, and the versatility and ease of their use. The microbubbles can be injected upstream of the target region, and then that target region is easily imaged at low intensity by the presence of the bubbles. When the imaging demonstrates that the ultrasound is precisely focused on the target tissue, then the ultrasonic intensity can be increased to create collapse cavitations. The collapse events appear to permeabilize the vessel walls and provide pathways for extravasation of DNA that is freely floating along with the bubbles, or that is associated with the bubble surface. (See Price R, Kaul S. Contrast Ultrasound Targeted Drug and Gene Delivery: An Update on A New Therapeutic Modality, J Cardiovasc Pharmascol Therapeut. 2002; 7(3): 171-180 and Miura S, Tachibana K, Okamoto T, Saku K. In Vitro Transfer of Antisense Oligodeoxynucleotides Into Coronary Endothelial Cells By Ultrasound. Biochem Biophys Res Commun. 2002; 298(4):587-590.) A convenient manner to prepare gene-carrying microbubbles is to insonate a mixture of surfactant in the presence of gas and the DNA fragment to be delivered. (See Teupe C, Richter S, Fisslthaler B, et al Vascular Gene Transfer of Phosphomimetic Endothelial Nitric Oxide Synthase (S1177d) Using Ultrasound-Enhanced Destruction Of Plasmid-Loaded Microbubbles Improves Vasoreactivity. (Circulation. 2002: 1104-1109.) If commercial contrast agents are available, the genetic material can be mixed directly with the contrast agent and injected (See Miura S, Tachibana K, Okamoto T, Saku K. In Vitro Transfer of Antisense Oligodeoxynucleotides into Coronary Endothelial Cells By Ultrasound. Biochem Biophys Res Commun. 2002; 298(4):597-590; Beeri R, Guerrero Jl, Supple G, Sullivan S, Levine Ra, Hajjar Rj. New Efficient Catheter-Based System for Myocardial Gene Delivery. Circulation. 2002; 106(14):1756-1759; and Endoh M, Koibuchi N, Sato M, et al. Fetal Gene Transfer By Intrauterine Injection with Microbubble-Enhanced Ultrasound. Molecular Therapy. 2002; 5(5):501-508.)

Micelles Vesicles and Liposomes:

A micelle is an aggregation of surfactant molecules dispersed in a liquid colloid. A vesicle is a small membrane-enclosed sack that can store or transport substances. Liposomes are artificially prepared vesicles made of lipid bilayer. They have been used for a long time as drug carriers, and recently as gene carriers. Ultrasound applied in combination with gene-carrying liposomes has enhanced the transfection rate both in vitro (See Unger Ee, Fritz Ta, Matsunaga T, Ramaswami Vr, Yellowhair D, Wu G: Therapeutic Drug Delivery Systems. In; U. S. Patent Database Imarx Pharmaceutical Corp; United States of America: (1996):48; Unger E C, McCreery T P, Sweitzer R H. Ultrasound Enhances Gene Expression of Liposomal Transfection. Investigative Radiology. 1997; 32(12):723-727; Lawrie A, Brisken A F, Francis Se, Et al. Ultrasound Enhances Reporter Gene Expression after Transfection of Vascular Cells In Vitro. Circulation. 1999; 99(20):2617-2620; and Mccreery T P, Sweitzer R H, Unger E C: DNA Delivery to Cells in Culture Using Ultrasound. In: Methods in Molecular Biology Vol. 245. Heiser We, Ed. Humana Press; Totowa, New Jersey: (2004):287-291.) and in vivo. (See Mccreery T P, Sweitzer R H, Unger E C: DNA Delivery To Cells In Vivo By Ultrasound. In: Methods In Molecular Biology Vol. 245. Heiser We, Ed. Humana Press; Totowa, New Jersey: (2004): 293-298.)

Free Genetic Material:

In the absence of microbubbles, liposomes, or other acoustically active agents, it is known that ultrasound can still enhance transfection (See Taniyama Y, Tachibana K, Hiraoka K, et al. Local Delivery of Plasmid DNA into Rat Carotid Artery Using Ultrasound. Circulation. 2002; 105 (10):1233-1239.) As an in vitro example, ultrasound without any extraneous cavitation agents increased transfection of human endothelial cells and vascular smooth muscle cells slightly (compared to a non-ultrasound control), whereas when microbubbles were present, the transfection increased by more than three orders of magnitude. (See Taniyama Y, Tachibana K, Hiraoka K, et al. Local Delivery of Plasmid DNA into Rat Carotid Artery Using Ultrasound. Circulation. 2002; 105(10):1233-1239.) This type of transfection is often attributed to sonoporation of cell membranes by acoustic activity, but the mechanisms leading to sonoporation in the absence of microbubbles are currently not well understood. Another known disadvantage of using free DNA is that ultrasound causes DNA fragmentation (See Riesz P, Kondo T. Free-Radical Formation Induced by Ultrasound and its Biological Implications. Free Radical Biology and Medicine. 1992; 13(3):247-270.) that reduces the transfection efficiency (See Guillaume C, Delepine P, Droal C, Montier T, Tymen G, Claude F. Aerosolization Of Cationic Lipid-DNA Complexes: Lipoplex Characterization And Optimization Of Aerosol Delivery Conditions. Biochem Biophys Res Commun. 2001; 286(3):464-471.}. Complexing the DNA plasmids with cationic polymers preserves the integrity of the DNA during exposure to 20 kHz ultrasound. (See Kuo J H S, Jan M S, Sung K C, Evaluation of the Stability of Polymer-Based Plasmid DNA Delivery Systems After Ultrasound Exposure. International Journal Of Pharmaceutics. 2003; 257(1-2):75-84.) Another strategy to protect the DNA is to expose the tissues to ultrasound and then subsequently perfuse the genetic material into the targeted region. (See Anwer K, Kao G, Proctor B, et al. Ultrasound Enhancement of Cationic Lipid-Mediated Gene Transfer to Primary Tumors Following Systemic Administration. Gene Therapy. 2000; 7(21): 1833-1839.)

Examples of Ultrasound-Assisted Gene Delivery

Ultrasound-enhanced gene delivery to cultured cells in vitro has been well reported. However, here the focus is on published reports of gene delivery to tissues in vivo.

Recent ultrasound-enhanced gene delivery research has focused on the combination of visualizing coronary arteries or other heart structures, and then delivering genes or drugs to the diseased tissues. (See Lindner J R. Microbubbles In Medical Imaging: Current Applications and Future Directions. Nature Reviews Drug Discovery. 2004; 3(6):527-532.) In most published studies a marker gene has been delivered to confirm efficacy of the concept. A long-term objective of cardiac gene delivery is to deliver genes that will inhibit or reverse stenosis of coronary arteries or to rejuvenate damaged/diseased/missing tissue.

Ultrasound-enhanced gene deliveries to arteries as a delivery system that can be used to treat stenosis and other arterial diseases have been reported. Both endovascular ultrasound and extracorporeal ultrasound have been studied and reported. For example, an endovascular ultrasonic catheter was employed in a rabbit femoral artery model of over dilation. (See Amabile P G, Waugh J M, Lewis T N, Elkins C J, Janas W, Dake M D. High-Efficiency Endovascular Gene Delivery Via Therapeutic Ultrasound. Journal of the American College of Cardiology. 2001; 37(7): 1975-1980.)

Genetic targeting of tumors as an anticancer therapy is an active research area, and several studies have been published on the feasibility of such a therapy. For example, MC38 murine colon carcinoma in mice was grown and was then injected directly into the tumor a naked plasmid with a reporter gene. (See Manome Y, Nakamura M, Ohno T, Furuhata H. Ultrasound Facilitates Transduction of Naked Plasmid DNA Into Colon Carcinoma Cells In Vitro And In Vivo. Human Gene Therapy. 2000; 11(11):1521-1528.) insonated Application of 1 MHz transcutaneous insonation increased the reporter activity 3-fold over the non-insonated control.

Skeletal muscle is one of the largest tissue systems in the body and it expresses several types of therapeutic proteins into the circulatory system to eventually find another target tissue, or to produce a "whole body" therapy. Other applications promote neovascularization for tissue repair. Several reports on ultrasound-enhanced gene delivery to skeletal muscles have been published.

Gene transfection on fetal mice m utero was reported using a plasmid encoding a fluorescent marker. (See Endoh M, Koibuchi N, Sato M, et al. Fetal Gene Transfer By Intrauterine Injection with Microbubble-Enhanced Ultrasound. Molecular Therapy. 2002; 5(5):501-508.) In this procedure, an incision was made on a pregnant mouse and the uterus externalized. Then plasmid mixed with microbubbles was delivered to specific locations by micropipette, the ultrasound applied, the uterus replaced, and the fetus developed for another 24 to 48 hours. Gene expression with naked DNA alone, DNA with microbubbles, or DNA with ultrasound was low and showed no significant difference between these conditions. However, application of 1 MHz ultrasound to plasmid and microbubbles produced about a 1000-fold enhancement in gene expression. Micrographs showed some disruption to the fetal skin under conditions of ultrasound with microbubbles. Expressing genes directly in the brain that may ameliorate debilitating brain diseases has important applications (i.e. Alzheimer's disease). Some reports on in vitro delivery to neural tissue in culture have been published. (See Barbarese E, Ho S-Y, D'arrígo J S, Simon R H. Internalization of Microbubbles by Tumor Cells In Vivo And In Vitro. Journal of Neuron-Oncology, 1995; 26:25-34.) and reports of employing ultrasound to breach the blood-brain barrier. (See W. E. Thomas, M. Forero, O. Yakovenko, L, Nilsson, P. Vicini, E. Sokurenko and V. Vogel, Catch-bond model derived from allostery explains force-activated bacterial adhesion, *Biophys. J.* 90 (2006), pp. 753-764; Cho C-W, Liu Y, Cobb W N, et al. Ultrasound-Induced Mild Hyperthermia as A Novel Approach to Increase Drug Uptake In Brain Micro vessel Endothelial Cells. Pharm Res. 2002; 19(8):1123-1129; Mesial Ah, Farrell L, Wenzel Haj, Et al. High-Intensity Focused Ultrasound Selectively Disrupts the Blood-Brain Barrier In Vivo, Ultrasound Med Biol. 2002; 28(3):389-400; Cho Cow, Liu Y, Cobb W N, Et al. Ultrasound-Induced Mild Hyperthermia as A Novel Approach To Increase Drug Uptake In Brain Micro vessel Endothelial Cells. Pharmaceutical Research. 2002; 19(8):1123-1129; Handymen K, Mcdannold N, Martin H, Jolesz Fa, Vykhodtseva N. The Threshold for Brain Damage In Rabbits Induced By Bursts Of Ultrasound In The Presence Of An Ultrasound Contrast Agent (Optison®). Ultrasound in Medicine and Biology. 2003; 29(3):473-481.) Lung tissue contains substantial amount of gas, therefore it reflects and scatters ultrasound; thus transcutaneous ultrasound cannot be used to deliver therapeutics to the lungs. An alternative use of ultrasound in gene delivery is to create an aerosol using an ultrasonic nebulizer. Cationic-DNA complexes have been delivered to mice, rats and Guinea pigs, and their lung epithelial cells transfected. (See Guillaume C, Delepine P, Droal C, Montier T, Tymen G, Claude F. Aerosolization Of Cationic Lipid-DNA Complexes: Lipoplex Characterization And Optimization Of Aerosol Delivery Conditions. Biochem Biophys Res Commun. 2001; 286(3):464-471; and Pillai R. Petrak K, Blezinger P, Et al. Ultrasonic Nebulization of Cationic Lipid-Based Gene Delivery Systems For Airway Administration. Pharm Res. 1998, 15(11):1743-1747.)

Some Current Needs in Gene Delivery:

An important need is for a better understanding of cavitation physics and ultrasound-microbubble interactions due to the recent progress in gene delivery involving microbubble cavitation. Another need is to develop better protection for the genetic material so that it is not degraded by fluid shear forces or enzymes before it can be delivered to the cells. In addition, the loading of genetic material needs to be optimized such that the genes are delivered only to the target tissues and not to tissues downstream from the insonated site.

Proteins are often differentiated from other macromolecules by their size (over 2000 Daltons of molecular weights) and characteristic polypeptide backbone. Smaller polypeptides can be treated as low molecular weight drugs. Compared to low molecular weight drugs, the proteins have very different transport and solubility characteristics in tissues. Consequently, their delivery is usually substantially more complex than smaller molecules. Specifically, proteins do not diffuse easily through solids and most gels. A simple bilayer lipid membrane is sufficient to preclude the transport of a protein. Two systems with large surface area, the skin and the gastrointestinal (GI) tract, are problematic. The skin is designed to be impermeable to protein transport, and the GI tract hydrolyses proteins into smaller peptides and amino acids for absorption. The high surface area of the lungs makes the pulmonary system attractive for protein delivery. However, lung tissue blocks ultrasound as previously mentioned. These issues limit most protein delivery to injection with some applications employing inhalation. Regulatory hormones are the center of focus for controlled protein delivery; specifically insulin delivery for diabetes therapy comprises the vast majority of protein delivery research, with some research effort in growth-related hormones and birth control hormones. With respect to ultrasound-assisted protein delivery, nearly all research is focused on insulin delivery, and the great majority of that research is on transdermal delivery. Ultrasonic delivery is useful because a focused or un-focused transducer can be placed on the skin surface for a painless, non-invasive delivery route.

Transdermal Drug Delivery:

The use of ultrasound to enhance the permeability of skin for transdermal drug delivery has been intensely studied. (See Mitragotri S, Kost J. Low-Frequency Sonophoresis. A Review. Adv Drug Deliv Rev. 2004; 56:589-601; Barry Bw. Novel Mechanisms and Devices to Enable Successful Transdermal Drug Delivery. European Journal of Pharmaceutical Sciences. 2001; 14:101-114; Prausnitz M R. Reversible Skin Permeabilization for Transdermal Delivery of Macromolecules. Critical Reviews in Therapeutic Drug Carrier Systems. 1997; 14(4):455-483; Guy R H. Current Status And Future Prospects of Transdermal Drug Delivery. Pharm Res. 1996; 13 (12):1765-1769; Kassan D G, Lynch Am, J Sm. Physical Enhancement of Dermatologic Drug Delivery—Iontophoresis and Phonophoresis. J Amar Accad Dermatology. 1996; 34(4):657-666; Bill N N. The Use of Ultrasound as an Enhancer for Transcutaneous Drug Delivery: Phonophoresis. Physical Therapy. 1995; 75(6):539-553; Tyle P, Agrawala P. Drug Delivery by Phonophoresis. Pharm Res. 1989; 6(5):355-361; and Skauen Din, Zentner G M. Phonophoresis. Int J Pharmaceutics. 1984; 20:235-245.) Therapeutic levels of ultrasound (1-3 MHz, 1-3 MHz W/cm$^2$) have been used for years to drive small hydrophobic molecules, such steroids, into or through the skin. (See Barry Bw. Novel Mechanisms and Devices To Enable Successful Transdermal Drug Delivery. European Journal of Pharmaceutical Sciences. 2001; 14:101-114; Prausnitz M R. Reversible Skin Permeabilization For Transdermal Delivery Of Macromolecules. Critical Reviews In Therapeutic Drug Carrier Systems. 1997; 14(4):455-483; Tyle P, Agrawala P. Drug Delivery By Phonophoresis. Pharm Res. 1989; 6(5): 355-361; Skauen Dm, Zentner G M. Phonophoresis. Int J Pharmaceutics. 1984; 20:235-245; Bommannan D, Okuyama H, Stauffer P, Guy R H. Sonophoresis. I The Use Of High-Frequency Ultrasound To Enhance Transdermal Drug Delivery. Pharm Res. 1992; 9(4):559-564; Bommannan D, Menon G K, Okuyama H, Elias P M, Guy R H. Sonophoresis. II Examination of the Mechanism(s) of Ultrasound-Enhanced Transdermal Drug Delivery. Pharm Res. 1992; 9(8):1043-1047; Menon O K, Bommannan D B, Elias P M. High-Frequency Sonophoresis: Permeation Pathways and Structural Basis for Enhanced Permeability. Skin Pharmacol. 1994; 7:130-139; and Vyas Sp, Singh R, Asati Rk. Liposomally Encapsulated Diclofenac for Sonophoresis Induced Systemic Delivery J Microencapsul. 1995; 12(2): 149-154.) Sometimes chemical enhancers were used to further increase the permeability. (See Mitragotri S. Synergistic Effect of Enhancers for Transdermal Drug Delivery. Pharm Res. 2000; 17(11):1354-1357; Johnson M E, Mitragotri S, Patel A. Blankschtein D, Langer R, Synergistic Effects of Chemical Enhancers and Therapeutic Ultrasound on Transdermal Drug Delivery. Journal of Pharmaceutical Sciences, 1946; 85(7):670-677; and Tezel A, Sens A, Tuchscherer J. Mitragotri A. Synergistic Effect of Low-Frequency Ultrasound and Surfactants on Skin Permeability. J Pharm Sci. 2002; 91(1):91-100.) However, no significant transport of protein could be achieved until when Mitrogotri and co-workers showed that low frequency ultrasound was much more effective than higher frequencies and provided evidence as to the mechanism involved. (Mitragotri S, Kost J. Low-Frequency Sonophoresis. A Review. Adv Drug Deliv Rev. 2004; 56:589-601.) Skin permeability increased with decreasing frequency, and with increasing time of exposure and intensity (beyond a threshold), thus identifying collapse cavitation as a causative mechanism. The current theory is that cavitation events open reversible channels in the lipids layers of the stratum corneum and provide less tortuous paths of transport for proteins such as insulin. Electron microscopy on skin exposed to low frequency ultrasound revealed the removal of surface cells and the formation of large pores and pockets (~20 μm), large enough to accommodate transport of proteins and other large molecules. (See Tezel A, Sens A, Tuchscherer J, Mitragotri A. Synergistic Effect of Low-Frequency Ultrasound and Surfactants on Skin Permeability. J Pharm Sci. 2002; 91(1):91-100; Wu J, Chappelow J, Yang J, Weimann L. Defects Generated In Human Stratum Corneum Specimens by Ultrasound. Ultrasound In Med & Biol. 1998; 24(5):705-710; Yamashita N, Tachibana K, Ogawa K, Tsujita N, Tomita A. Scanning Electron Microscopic Evaluation of The Skin Surface After Ultrasound Exposure. Anatom Rec. 1997; 247:455-461; Tezel A, Mitragotri S. On The Origin of Size-Dependent Tortuosity for Permeation of Hydrophilic Solutes Across the Stratum Corneum. Journal Of Controlled Release. 2003; 86(1):183-186; and Tezel A, Sens A, Mitragotri S. Description of Transdermal Transport of Hydrophilic Solutes During Low-Frequency Sonophoresis Based on A Modified Porous Pathway Model. 2003; 92(2):381-393.) The future of ultrasound-enhanced transdermal protein delivery is brimming with potential, but it has not yet appeared in the clinic. Because large pores and channels are opened through the natural skin barriers, many hormones and proteins could be candidates for transdermal delivery. The effect of the ultrasound on the protein conformation and/or activity needs to be addressed in more detail.

Insulin-loaded drug depots of poly(2-hydroxyethyl methacrylate) and poly(ethylene glycol) with a surface layer of C-18 alkyl chains has been studied, (See Kwok C S, Mourad P D, Crum L A, Ratner B D, Self-Assembled Molecular Structures As Ultrasonically-Responsive Barrier Membranes for Pulsatile Drug Delivery. J Biomed Mater Res. 2001; 57:151-164.) In the absence of insonation, the alkyl chains appeared to form an organized and less permeable barrier to proteins; upon insonation, the surface organization was apparently disrupted and protein within the depot matrix escaped, in their research very little insulin was released until 1.1-MHz ultrasound was applied. Upon termination of insonation the low permeability of the lipid-like surface layer was restored. A device based on a subcutaneous depot with an external (focused or un-focused) transducer positioned over the depot that can be activated either automatically or on demand as insulin has been discussed.

It is reported that the transport of tissue plasminogen activator and other lytic proteins such as urokinase into clots is beneficial in increasing the rate of fibrinolysis of clots. (See Francis C W, Onundarson P T, Carstensen El, et al. Enhancement of Fibrinolysis In Vitro By Ultrasound. J Clin Invest. 1992; 90(11):2063-2068; and Lauer C G, Burge R, Tang D B, Bass B G, Gomez Er, Alving Bm. Effect of Ultrasound On Tissue-Type Plasminogen Activator-Induced Thrombolysis. Circulation. 1992; 86:1257-1264.) In most studies, the protein is delivered to the clot via intravenous catheter, and the ultrasound is applied transdermally. Another advance in this technology is to attach receptors for the thrombus material to the microbubbles, thus attaching the bubble to the thrombus surface during the ultrasonic exposure. Often these ligands bind to the GPilb/Illa receptor of platelets which are expressed when platelets coalesce into a clot, and are used with or without a thrombolytic protein present. (See Wu Y Q, Unger E C, Mccreery T P, et al. Binding And Lysing of Blood Clots Using Mrx-408. Investigative Radiology. 1998; 33(12):880-885; and Culp W C, Porter T R, Lowery J, Roberson P K, Xie F. Mccowan T C Intracranial Clot Lysis With Intravenous Platelet Targeted Microbubbles And Transcranial Ultrasound. Circulation. 2003; 108(17):604-604.) It is envisioned that bubbles cavitating on the thrombus surface will produce micro-jets that can mechanically disrupt the clot.

Protein delivery to the lungs via inhalation of ultrasonically aerosolized protein solutions have been reported in the literature. Nebulization requires rather severe cavitation, therefore it is beneficial to protect the proteins by the addition of certain surfactant stabilizers. These additives appear to complex with the proteins and protect them from degradative shear stresses and probably from free radical attack. It is possible that the surfactants may form micelles or liposomes that sequester the proteins and protect them from cavitation stresses.

Current Trends in Protein Delivery:

Protein delivery is currently fairly limited by very slow diffusion of proteins through skin and polymeric depots, and by the proteinolysis that occurs in the upper human gastrointestinal tract. There has been a clear need for technology in which a polymeric depot can be implanted, and timed drug release could by activated by transdermal ultrasound. Polymers in a depot can be degraded by ultrasound (See Kost J. Ultrasound for Controlled Delivery of Therapeutics, Clinical Materials. 1993; 13:155-161), but this is a fairly slow process, and the same physicochemical mechanisms that degrade the polymers may degrade the proteins in the depot. Technology that will open and close the depot to protein transport is needed. It would also be advantageous if the depot is activated by stable cavitation or some other low intensity phenomenon related to ultrasound. Collapse cavitation may be capable of opening depots, but repeated ultrasonic exposure over long periods may start to have adverse effects on the healthy tissue in the region of the depot. Finally it would be beneficial if the depot were eventually degradable so that it did not need to be surgically removed when it was emptied.

Ultrasound-Enhanced Small Molecule Chemical Delivery

In the last three decades or so, ultrasound has been investigated as a delivery mechanism for a variety of therapeutic agents to diseased cells throughout the body. The use of ultrasound as a drug release and potentiation mechanism in traditional chemotherapy has been studied extensively. A synergistic effect between the pharmacological activity of chemotherapeutic drugs and ultrasound has been reported for a variety of agents. It has been shown that one hour of exposure to ultrasound (at the power intensity of 2.3 W/cm$^2$ at 2.6 MHz) rendered Doxorubic insignificantly more toxic to Chinese hamster lung fibroblasts. (See Loverock P, Ter Haarg, Ormerod M G, Imrie P R. The Effect of Ultrasound on the Cytoxicity of Adriamycin. Brit J Radiol. 1990; 63:542-546.) Exposure to ultrasound alone did not affect cell viability. Flow cytometry revealed an increase in Doxorubicin concentration inside the cells, but the authors did not attribute the increased uptake to any particular mechanism. Ultrasound has been used in combination with chemotherapeutic agents for increased efficacy, Insonation appears to enhance the transport of drugs into cells and tissues. Considering the physics of cavitation processes, ultrasound produces transient micropores in the cell membrane, which would increase the passive accumulation of the drugs in the cells and tissues. Although the cytotoxic effect of chemotherapeutic agents has been shown to increase with insonation, this effect has not been shown to be independent of any increase in drug uptake. Most data reported in literature support the hypothesis that ultrasound permeabilizes the membrane so that more chemotherapeutic drug molecules are able to diffuse into the cells. In some cases, the permeabilization appears truly synergistic in that both drug and ultrasound are required simultaneously to render the cell membrane more permeable. In general, though, at sufficiently high intensities the ultrasound permeabilizes the membrane, most probably through shear stresses in the membrane from microstreaming or shock waves. A current problem associated with whole body chemotherapy is not totally alleviated by ultrasound; the drug is still delivered systemically thus causing systemic side effects. For this reason, research in recent years has focused on developing molecular vehicles that can sequester the drug inside a package and then release it using ultrasound stimulus at the tumor site.

Image Enhancing Contrast Agents

Contrast-enhanced ultrasound is the application of ultrasound contrast medium to traditional medical sonography. Ultrasound contrast agents rely on the different ways in which sound waves are reflected from interfaces between substances. This interface may be the surface of a small air bubble or a more complex structure, Commercially available contrast media are gas-filled microbubbles that are administered intravenously to the systemic circulation. Microbubbles have a high degree of acoustic mismatch, which significantly increases their reflectivity, and therefore their contrast (See McCulloch, M., C. Gresser, S. Moos, J. Odabashian, S. Jasper, J. Bednarz, P. Burgess, D. Carney, V. Moore, E. Sisk, A. Waggoner, S. Witt, and D. Adams. Ultrasound contrast physics: A series on contrast echocardiography. J Am Soc Echocardiogr. 13:10, pp. 959-67, 2000.). Various materials have been used, including Microspheres of human albumin, Microparticles of galactose, Perflenapent, Microspheres of phospholipids, and Sulfur hexafluoride.

MRI contrast agents are a group of contrast media used to improve the visibility of internal body structures in magnetic resonance imaging (MRI). The most commonly used compounds for contrast enhancement are gadolinium-based. Others include iron oxide, ferric ammonium citrate various nanoparticles, MRI contrast agents alter the relaxation times of tissues and body cavities where they are deposited. Depending on the image weighting, this can give a higher or lower signal. (See Harisinghani, Mukesh G.; Weissleder, Ralph; Schima, Wolfgang; Saini, Sanjay; Hahn, Peter F.; Mueller, Peter R. (2001), MRI Contrast Agents for Evaluating Focal Hepatic Lesions. 56, Clinical Radiology, pp. 714-725).

Radio contrast agents are a type of medical contrast medium used to improve the visibility of internal bodily structures in an X-ray based imaging techniques such as Computed tomography (CT) or Radiography (commonly known as X-ray imaging). Radio contrast agents are typically iodine or barium compounds. Ionic contrast media have higher osmolarity and more side-effects, such as Urografin, Telebrix, Gastrografin, etc. Non-ionic contrast media, have lower osmolarity and tend to have less side-effects, such as Omnipaque, Ultravist, Visipaque, etc. Barium sulfate is mainly used in the imaging of the digestive system. The substance exists as a water insoluble white powder that is made into a slurry with water and administered directly into the gastrointestinal tract. (See Contrast Agents II: Optical, Ultrasound, X-Ray Imaging and Radiopharmaceutical Imaging (Topics in Current Chemistry, Werner Krause (Editor, 2010, Springer).

SUMMARY

An object of the preferred embodiment of the invention to disclose a method, device and system for ultrasonic delivery of ligand-receptor based drugs and image enhancing contrast agents utilizing catch and slip bonds in a targeted part(s) of the patient's body or organs are described and disclosed. One of the objects of utilizing catch and slip bonds in target part(s) of the patient's body is to substantially reduce or eliminate cavitation and other side-effects associated with drugs and agents in the process.

The exemplary embodiment is a method of using a system of ultrasonic delivery of drugs and/or drug carriers and/or imaging contrast agents. The system includes an acoustic power source coupled to an acoustic transducer with the acoustic transducer placed upon a patient's drug/agents delivery zone. The acoustic transducer transmits an acoustic field to the delivery zone. A detection probe is placed over the delivery zone. The probe is coupled to a sensing or imaging system. A control computer controls the acoustic power source and receives data from said sensing system the method of ultrasonic delivery.

The method includes placing an acoustic transducer over a delivery zone having drugs and/or drug carriers and/or imaging contrast agent, and coupling an acoustic power source to said acoustic power source.

A probe is installed within or over said delivery zone and is coupled to a sensing or imaging system. An output of the sensing/imaging system to the computer to calculate results of said ultrasonic delivery of said drugs and contrast agents and to provide corrective control of said power, focusing, duty cycle and wave shape of said acoustic field.

A control computer is used to control power, focusing, duty cycle and wave shape of the acoustic field generated by the acoustic transducer. The system utilizes catch and slip bonds within said acoustic field to deliver drugs and/or drug carriers and/or imaging contrast agent.

This Summary is provided merely to introduce certain concepts and to identify any key or essential features of the claimed subject matter.

BRIEF DESCRIPTION OF THE DRAWINGS

These and other features, aspect, and advantages of the present invention will become better understood with regard to the following description, appended claims, and accompanying drawings where:

FIG. 1 (B) illustrates the dependence of the lifetime of receptor-ligand interactions on the force level in slip bonds;

FIG. 1 (C) illustrates the dependence of the lifetime of receptor-ligand interactions on the force level in catch bonds;

FIG. 2 (B) illustrates the accumulation of type 1 fimbriated *E. coli* on a mannosylated surface, dependent on shear level;

FIG. 2(C) illustrates the lifetime of P-selectin-PSGL-1 bonds, dependent on the level of tensile force applied by AFM;

DETAILED DESCRIPTION

Introduction

A method, device and system for ultrasonic delivery of ligand-receptor based drugs and/or drug carriers and/or imaging contrast agents utilizing catch and slip bonds in a targeted part(s) of the patient's body or organs are described and disclosed. The approach is based on the experimental fact that the strength and/or lifetime of certain classes of ligand-receptor bonds (catch and slip bonds) are enhanced or shortened by external stress, moment and/or strains on the bond. Biological or man-made objects (e.g. drug carriers containing drugs such as micro/nano-particles, microbubbles, liposomes, micelles, vesicles, and free genetic materials) with a receptor that can form a catch bond with its ligand(s) can be attached to surfaces containing these ligand(s) in a specific range of external forces and moments creating a strain (stress) level in the bond. Below the lower bound and above the upper of this range in a catch bond the bonding is unlikely and/or with very short lifetimes. In many cases, the external stress/moment/strain on the bond is exerted by a shear field generated by fluid flow, such as blood circulation, Slip bonds, weakened as a result of an external mechanical effect, are utilized to detach a drug carrier. In the embodiment(s) described herein, the required external stress/moment/strain is ultrasonically applied to a delivery zone in the patient's body or organ that is targeted for drug therapy and/or medical imaging as the drug loaded objects (i.e. drug carriers) and/or imaging contrast agents with engineered receptors or ligands are circulated in the blood or interstitial fluids or tissue. These objects upon attachment which is controlled by a catch bond begin delivering drug and/or imaging agents either automatically and/or by an external source (such as an ultrasonic field, chemical enhancer, etc.). Their detachment (if need be) can be realized by activating slip bonds by an ultrasonic field with a set of certain characteristics (e.g. frequency, amplitude (power, duration, duty cycle, etc.). Similarly, two or more circulated objects in the circulation system can also be activated to bond or de-bond in a non-contact manner in a controllable fashion. These bonded composite drug carrier objects and/or contrast agents (e.g. large molecules, large molecule coated particles, drug bubbles, etc.) can also be attached (or detached) to the target zone using the same mechanism, or automatically attaches (detaches) to (from) their target zones.

System Description:

An embodiment of the system is described, and various other embodiments are detailed and discussed. A preferred embodiment of the design involving a high frequency programmable computer-controlled power source (0.1-20 MHz at 0-20 Watts/cm$^2$ with application durations from a few seconds to hours with a specified duty cycle) with a focusing ultrasonic transducer is described, and various other embodiments are detailed herein.

Figure 1:
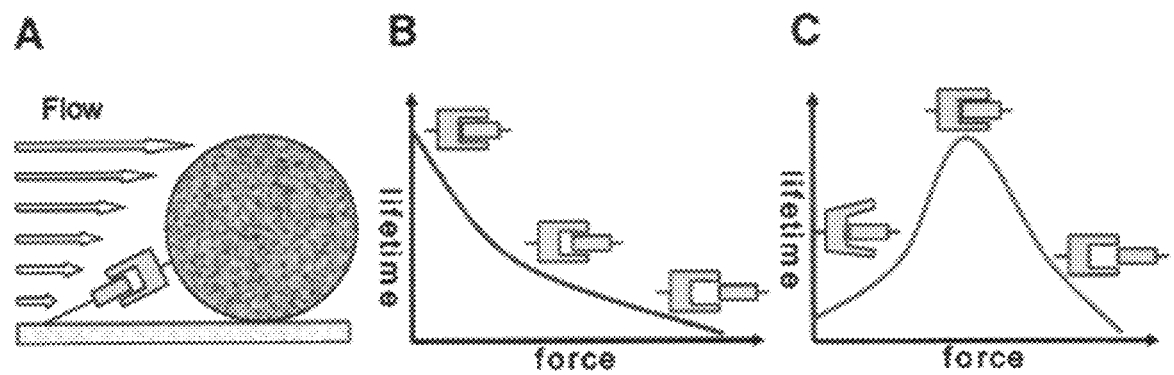
FIG. 1 (A) illustrates a schematic presentation of drag (shear) force on an adhering cell.
Figure 2:
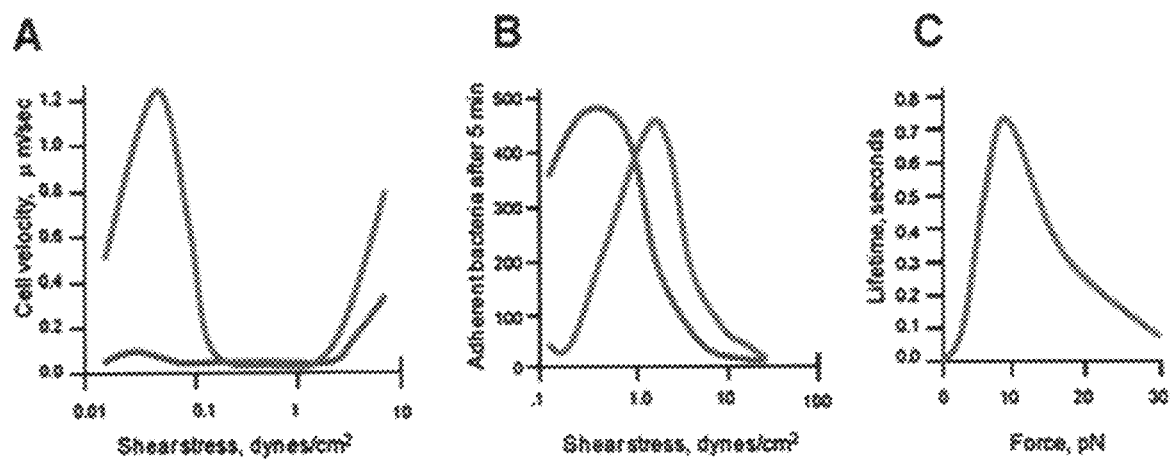
FIG. 2 (A) illustrates the rolling velocity of red blood cells over a carpet of type 1-fimbriated *E. coli*, dependent on shear level).
Figure 3:
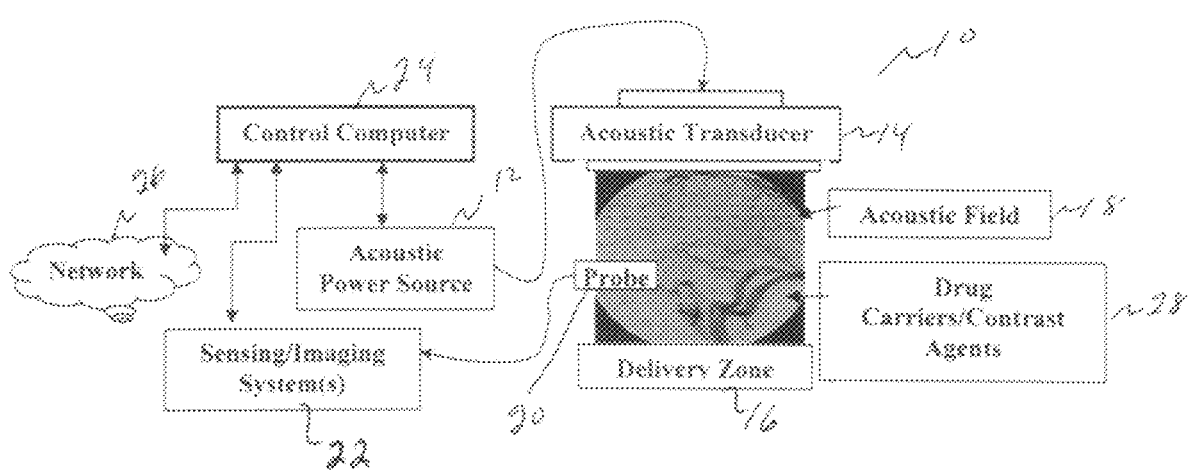
FIG. 3 illustrates a schematic of the described drug delivery/contrast agents device and system.
Figure 4:
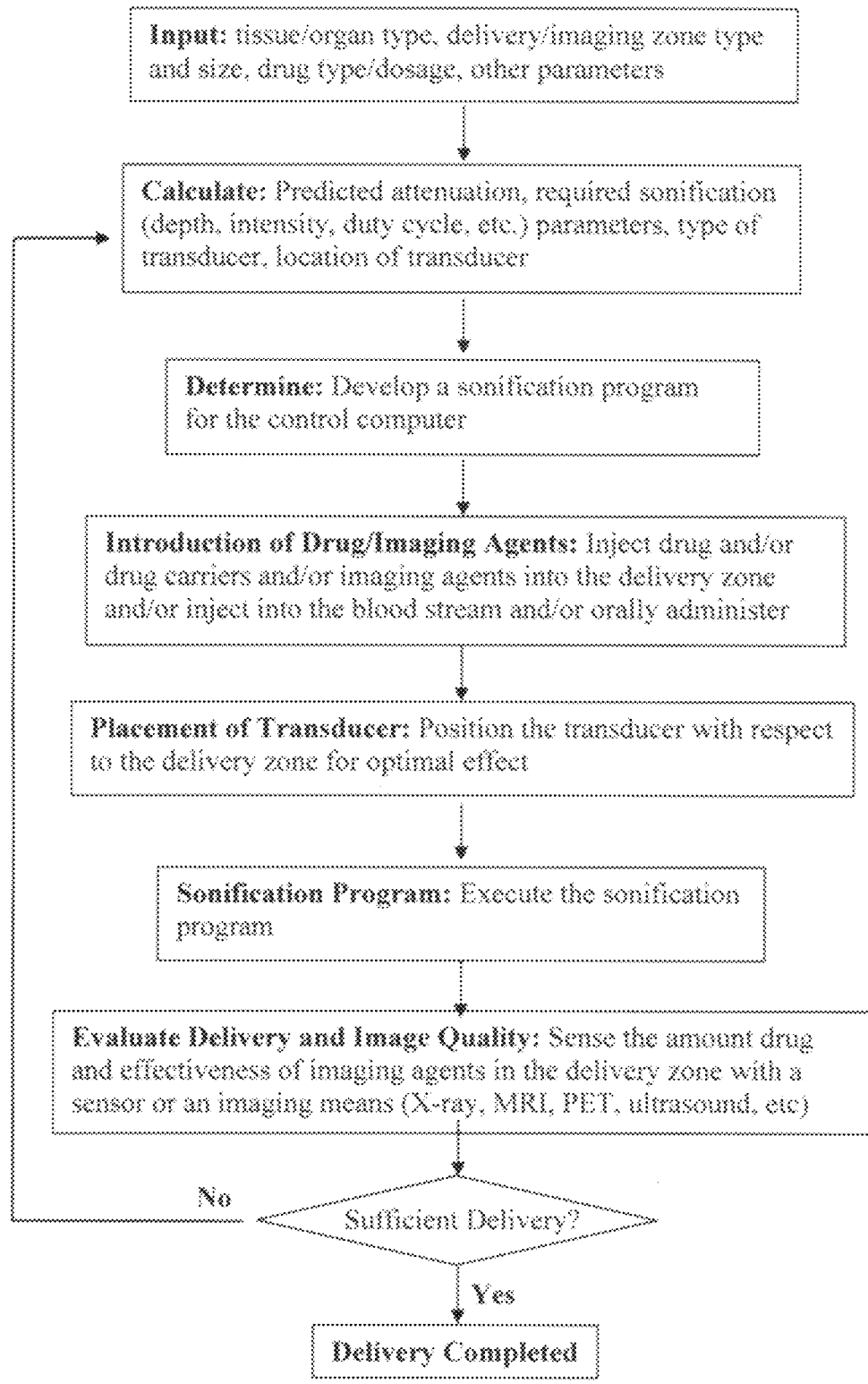
FIG. 4 illustrates a flow diagram of the method of drug/contrast agents delivery.

Included is a sonification time program controlling attachment and detachment cycles, and a sensing system (with a probe/sensor head) or an imaging system (X-ray CT, MRI, PET, ultrasound, etc.) for closing the delivery loop by assessing effectiveness and efficacy as depicted in FIG. 3 (Schematic) and FIG. 4 (FlowChart). The interfaced control computer includes a delivery program with the power specification, duty cycle and sonification time program depending upon the patient and drug specifics. This control computer is networked, so remote monitoring and control of the described method, device, and system is possible. The acoustic power source provides electrical energy in the form of a pulse into the acoustic transducer according to the therapy program stored in the control computer. Drug carriers are introduced into the blood stream by well-established techniques. Most common routes of administration include the non-invasive peroral (through the mouth), topical (skin), inhalation routes and transmucosal (nasal, buccal, sublingual, vaginal, ocular and rectal). The acoustic transducer converts the electrical energy into mechanical (acoustic) energy and delivers the required acoustic field that controls the delivery and detachment of drug carriers and contrast agents into to the drug/contrast agents delivery zone according to the therapy program. The acoustic field modifies the properties of the catch and slip bond between the drug delivering zone and the drug carriers. The sensing system with the help of its probe measures the level of delivered drug to the delivery zone and/or other physiological responses of the patient's body and transmits this information to the control computer. The control computer can report this information to the health care provider for further decisions and/or modifications in the delivery program.

The system, as illustrated in FIG. 3, for ultrasonic delivery of drugs and contrast agents 10 includes: an acoustic power source 12 coupled to an acoustic transducer 14 that is placed over a patient's delivery zone 16; the acoustic transducer 14 transmits an acoustic field 18 to the delivery zone 16; a detection probe 20 is placed over or within the delivery zone 16; the probe 20 is coupled to sensing and imaging systems 22; and a control computer 24 that controls the acoustic power source 12 and receives data from the sensing system 22. A network 26 is coupled to the control computer for remote observation and/or control of the system. The system uses drug carriers such as catch and slip bonds for the delivery of drug and/or drug carriers and/or imaging contrast agents Since the disclosed approach requires lower levels of power radiations, the associated instruments and transducers are subjected to less heating and, consequently, relatively lower cost. Due to low power requirements, the described equipment may be subjected to a lower level of legal scrutiny and less strict regulations.

Method Description

The method of using a system for ultrasonic delivery of drugs, as described above includes: placing an acoustic transducer over a patient's drug and/or drug carriers and/or imaging contrast agents delivery zone having drug carriers; then coupling an acoustic power source to the acoustic power source; installing a probe within or over the delivery zone; coupling the probe to a sensing system; using a control computer to control a power and a wave shape of the acoustic field generated by the acoustic transducer; utilizing catch and slip bonds within the acoustic field to deliver drug and/or drug carriers and/or imaging contrast agents; coupling an output of the sensing/imaging system to the computer to calculate results of the ultrasonic delivery and to provide corrective feedback of the power and wave shape of the acoustic field.

FIG. 4 illustrates a flow diagram of the method of a using a system for delivering drug and/or drug carriers and/or imaging contrast agents as described above. The computer program within the computer is programmed to accept tissue/organ types, delivery zone types and size, drug type/dosage and other parameters so that the user may input the particular parameters in the procedure being used. From this data, the computer calculates the predicted attenuation, the required sonification parameters (depth, intensity, duty cycle and other relevant parameters, type of transducer and location of the transducer). The operator selects the proper sonification program within the computer. After these preparatory steps there is an injection of drug and/or drug carriers and/or imaging contrast agents into the delivery zone and/or inject them into the blood stream and/or they are orally administered. The transducer is positioned with respect to the delivery zone for optimal delivery. The sonification program is then executed by the control program. An evaluation of the delivery including a sense of the amount of drug and imaging contrast agents in the delivery zone with sensors and/or an imaging means such as X-ray, MRI, PET or ultrasound. If it is determined that there has been sufficient delivery of drug and/or drug carriers and/or imaging contrast agents, the delivery is completed. If there has been insufficient delivery, one or more of the steps in the flowchart are to be repeated.

Controllable Attachment and Detachment:

By utilizing catch and slip bonds in delivery as described in this disclosure, drug carriers and/or imaging contrast agents can not only be delivered to a particular zone in a controllable manner, but it (in part or whole) can also be detached from the zone at will. This approach limits the total amount of drug administered to the body for therapy, and minimizes various adverse effects such as drug overdose, dosage-related side effects, clog, blockage, and aggregation of drug carriers.

Minimal or No Cavitation is Required.

The current ultrasonic drug delivery techniques and technologies are typically based on cavitation based mechanisms. Cavitation is the formation and/or activity of gas-filled bubbles in a medium exposed to ultrasonic waves. As the pressure wave passes through the media, gas bubbles of any size will expand at low pressure and contract at high pressure. If the resulting oscillation in bubble size is fairly stable, the cavitation is called stable or non-inertial cavitation. As the ultrasonic intensity increases, the amplitude of oscillation also increases to a point in at which the inward moving wall of fluid has sufficient inertia that it cannot reverse direction when the acoustic pressure reverses, but continues to compress the gas in the bubble to a very small volume, creating extremely high pressures and temperatures. This type of cavitation can be detrimental to cells or vesicles because of the very high shear stresses in the region of the collapse, the shock waves produced by the collapse, and the free radicals produced by the high temperatures. While various processes associated with cavitation in drug delivery, in general, drug delivery is achieved by violent thermo-mechanical forces. It is not always possible to predict these forces and/or to control their side-effects. In fact, damage to cells, tissues and large molecules (e.g. DNA fragmentation) due to cavitation has been reported in the literature. The described approach based on ultrasonic activation of catch bonds is significantly gentler due to the lower required force levels since its mechanism is based on promoting the ligand-receptor bonds, rather than destructively opening structural channels in cells and tissues and/or breaking large molecules for drug delivery.

Formation of Bonds is Promoted:

Unlike cavitation-based ultrasonic drug delivery, the disclosed technique promotes the formation of bonds. The described delivery mechanism opens up new possibilities for some large molecule drugs that cannot be delivered with prior methods.

It is thought that method and apparatus for ultrasonic delivery of drug and/or drug carriers and/or imaging contrast agents of the present invention and many of its attendant advantages will be understood from the foregoing description and that it will be apparent that various changes may be made in the form, construction, and arrangement of the parts without departing from the spirit and scope of the invention or sacrificing all of its material advantages, the form hereinbefore described being a preferred or exemplary embodiment thereof.

LIST OF REFERENCES

1. G. I. Bell, Models for the specific adhesion of cells to cells, Science 200 (1978), pp. 618-627.
2. M. Dembo, D. C. Toney, K. Saxman and D. Hammer, The reaction-limited kinetics of membrane-to-surface adhesion and detachment, Proc. R. Soc. Land. B. Biol. Sci. 234 (1988), pp. 55-83.
3. W. E. Thomas, E. Trintchina, M. Forero, V. Vogel and E. V. Sokurenko, Bacterial adhesion to target cells enhanced by shear force, Cell 109 (2002), pp 913-923.

4. B. T. Marshall, M. Long, J. W. Piper, T. Yago, R. P. McEver and C. Zhu, Direct observation of catch bonds involving cell-adhesion molecules, *Nature* 423 (2003), pp. 190-193.
5. P. Robert, A Benoliel, A. Pierres, and P. Bondrand, *What is the biological relevance of the specific bond properties revealed by single molecule studies?*, J. of Molecular Recognition, 20, pp. 432-447, 2007.
6. P. F. Davies, Flow-mediated endothelial mechanotransduction, *Physiol. Rev.* 75 (1995), pp. 519-560.
7. Z. Guo, M. Moreau, D. W. Rickey, P. A. Picot and A. Fenster, Quantitative investigation of in vitro flow using three-dimensional colour Doppler ultrasound, *Ultrasound Med. Biol.* 21 (1995), pp. 807-816.
8. V. Vogel and M. Sheetz, Local force and geometry sensing regulate cell functions, *Nat. Rev. Mal. Cell Biol.* 7 (2006), pp. 265-275,
9. E. Evans and K. Ritchie, Dynamic strength of molecular adhesion bonds, *Biophys. J.* 72 (1997), pp. 1541-1555.
10. Evgeni V. Sokurenko, Viola Vogel and Wendy E. Thomas, Catch-Bond Mechanism of Force-Enhanced Adhesion: Counterintuitive, Elusive, but . . . Widespread?, Cell Host and Microbe, Volume 4, Issue 4, 16 Oct. 2008, Pages 314-323
11. E. B. Finger, K. D. Puri, R. Alon, M. B. Lawrence, U. H. von Andrian and T. A. Springer, Adhesion through L-selectin requires a threshold hydrodynamic shear, *Nature* 379 (1996), pp. 266-269.
12. W. E. Thomas, E. Trintchina, M. Forero, V. Vogel and E. V. Sokurenko, Bacterial adhesion to target cells enhanced by shear force, *Cell* 109 (2002), pp. 913-923.
13. B, Savage, E. Saldivar and Z. M. Ruggeri, Initiation of platelet adhesion by arrest onto fibrinogen or translocation on von Willebrand factor, *Cell* 84 (1996), pp. 289-297.
14. K. C. Chang and D. A. Hammer, The forward rate of binding of surface-tethered
15. reactants: effect of relative motion between two surfaces, *Biophys. J.* 76 (1999), pp. 1280-1292
16. S. Chen and T. A. Springer, An automatic braking system that stabilizes leukocyte rolling by an increase in selectin bond number with shear, *J. Cell Biol.* 144 (1999), pp. 185-2).
17. S, Lu, Z. Ye, C. Zhu and M, Long, "Quantifying effects of contact duration, loading rate, and approach velocity on P-selectin-PSGL-1 interactions using AFM," *Polymer* 47, 2539 (2006).
18. Y. Pereverzev, O. V. Prezhdo, M. Forero, E. Sokurenko and W. Thomas, The Two-Pathway Model for the Catch-Slip Transition in Biological Adhesion, *Biophys. J.* 89 (2005), pp. 1446-1454.
19. Y. V. Pereverzev, O. V. Prezhdo, W. E. Thomas and E. V. Sokurenko, Distinctive features of the biological catch bond in the jump-ramp force regime predicted by the two-pathway model, *Phys. Rev. E Stat. Nonlin. Soft Matter Phys.* 72 (2005), p. 010903.
20. Y. Pereverzev and O. Prezhdo, Force-Induced Deformations and Stability of Biological Bonds, *Phys. Rev. E Stat. Nonlin. Soft Matter Phys.* 73 (2006), p. 050902.
21. J. Lou, T. Yago, A. G. Klopocki, P. Mehta, W. Chen, V. I. Zarnitsyna, N. V. Bovin, C. Zhu and R. P. McEver, Flow-enhanced adhesion regulated by a selectin interdomain hinge, *J. Cell Biol.* 174 (2006), pp. 1107-1117.
22. B. H. Luo, K. Strokovich, T. Walz, T. A. Springer and J. Takagi, Allosteric beta1 integrin anti-bodies that stabilize the low affinity state by preventing the swing-out of the hybrid domain, *J. Biol. Chem.* 279 (2004), pp. 27466-27471.
23. W. E. Thomas, M. Forero, O. Yakovenko, L. Nilsson, P. Vicini, E. Sokurenko and V. Vogel, Catch-bond model derived from allostery explains force-activated bacterial adhesion, *Biophys. J.* 90 (2006), pp. 753-764.
24. O. Yakovenko, S. Sharma, M. Forero, V. Tchesnokova, P. Aprikian, B. Kidd, A. Mach, V. Vogel, E. Sokurenko and W. Thomas, FimH forms catch bonds that are enhanced by mechanical force due to allosteric regulation, *J. Biol. Chem.* 283 (2008), pp. 11596-11605.
25. V. Barsegov and D. Thirumalai, Dynamics of unbinding of cell adhesion molecules: transition from catch to slip bonds, *Proc. Natl. Acad. Sci. USA* 102 (2005), pp. 1835-1839.
26. E. Evans, A. Leung, V. Heinrich and C. Zhu, Mechanical switching and coupling between two dissociation pathways in a P-selectin adhesion bond, *Proc. Natl. Acad Sci. USA* 101 (2004). pp. 11281-11286.
27. William G. Pitt, Ghaleb A. Husseini, And Bryant J. Staples, Ultrasonic Drug Delivery—A General Review, Expert Opin Drug Deliv. 2004 November; 1(1): 37-56.
28. Unger E, Porter T, Culp W, Labell R, Matsunaga To, Zutshi R. Therapeutic Applications of Lipid-Coated Microbubbles. Adv Drug Deliv Rev. 2004; 56(9):1291-1314.
29. Stride E, Saffari N. The Potential for Thermal Damage Posed by Microbubble Ultrasound Contrast Agents. Ultrasonics, 2004; 42(1-9):907-13.
30. Schutt E H, Klein D H, Mattrey Rm, Riess J G. Injectable Microbubbles as Contrast Agents for Diagnostic Ultrasound imaging: The Key Role Of Perfluorochemicals. Angewandte Chemie—International Edition. 2003; 42(28):3218-3235.
31. Niidome T, Huang L. Gene Therapy Progress And Prospects: Nonviral Vectors. Gene Therapy. 2002; 9(24): 1647-1652.
32. Price R, Kaul S. Contrast Ultrasound Targeted Drug and Gene Delivery: An Update on A New Therapeutic Modality. *J. Cardiovasc Pharmascol Therapeut.* 2002; 7(3):171-180.
33. Lindner L, Eichhorn Me, Eibl H. et al, Novel Temperature-Sensitive Liposomes with Prolonged Circulation Time. Clinical Cancer Research. 2004; 10(6):2168-2178.
34. Miller D. Pislaru Sv, Greenleaf J. Sonoporation: Mechanical DNA Delivery By Ultrasonic Cavitation. Somatic Cell Molec Genetics. 2002; 27(1):115-134.
35. Shohet R V, Chen S, Zhou Y-T, et al. Echocardiographic Destruction of Albumin Microbubbles Directs Gene Delivery to The Myocardium. Circulation. 2000; 101: 2554-2556.
36. Lawrie A. Brisken A F, Francis Se, Cumberland De, Crossman De, Newman Cm. Microbubble-Enhanced Ultrasound for Vascular Gene Delivery. Gene Ther. 2000; 7(23):2023-2027.
37. Miura S, Tachibana K, Okamoto T, Saku K. In Vitro Transfer of Antisense Oligodeoxynucleotides Into Coronary Endothelial Cells By Ultrasound. Biochem Biophys Res Commun. 2002; 298(4):587-590.
38. Teupe C, Richter S, Fisslthaler B, et al. Vascular Gene Transfer of Phosphomimetic Endothelial Nitric Oxide Synthase (S 1177d) Using Ultrasound-Enhanced Destruction Of Plasmid-Loaded Microbubbles Improves Vasoreactivity. Circulation. 2002: 1104-1109.
38. Beeri R, Guerrero J I, Supple G, Sullivan S, Levine Ra, Hajjar Rj. New Efficient Catheter-Based System for Myocardial Gene Delivery. Circulation, 2002; 106(14):1756-1759, 39. Endoh M, Koibuchi N, Sato M, et al. Fetal Gene Transfer by intrauterine Injection with Microbubble-Enhanced Ultrasound. Molecular Therapy. 2002; 5(5):501-508.
40. Unger Ee, Fritz Ta, Matsunaga T, Ramaswami Vr, Yellowhair D, Wu G; Therapeutic
41. Drug Delivery Systems. In: U.S. Patent Database lmarx Pharmaceutical Corp; United States Of America: (1996): 48.
42. Unger E C, Mccreery T P, Sweitzer R H. Ultrasound Enhances Gene Expression of Liposomal Transfection. Investigative Radiology. 1997; 32(12):723-727.
43. Lawrie A, Brisken A F, Francis Se. Et al. Ultrasound Enhances Reporter Gene Expression after Transfection of Vascular Cells In Vitro. Circulation. 1999; 99(20):2617-2620.
44. Mccreery T P, Sweitzer R H, Unger E C: Dna Delivery To Cells In Culture Using Ultrasound. In: Methods In Molecular Biology Vol. 245. Heiser We, Ed, Humana Press; Totowa, New Jersey: (2004):287-291.
45. McCreery T P, Sweitrer R H, Unger E C: Dna Delivery To Cells In Vivo By Ultrasound. In: Methods In Molecular Biology Vol. 245. Heiser We, Ed. Humana Press; Totowa, New Jersey: (2004):293-298.
46. Taniyama Y, Tachibana K. Hiraoka K, et al, Local Delivery of Plasmid DNA into Rat Carotid Artery Using Ultrasound, Circulation. 2002; 105(10):1233-1239.
47. Riesz P, Kondo T. Free-Radical Formation Induced By Ultrasound and Its Biological Implications, Free Radical Biology and Medicine. 1992; 13(3):247-270.
48. Kuo J H S, Jan M S, Sung K C. Evaluation of the Stability Of Polymer-Based Plasmid
DNA Delivery Systems After Ultrasound Exposure. International Journal Of Pharmaceutics. 2003; 257(1-2):75-84.
49. Anwer K, Kao G. Proctor B, et al. Ultrasound Enhancement of Cationic Lipid-Mediated Gene Transfer to Primary Tumors Following Systemic Administration. Gene Therapy. 2000; 7(21): 1833-1839.
50. Lindner J R. Microbubbles in Medical Imaging: Current Applications and Future Directions, Nature Reviews Drug Discovery. 2004; 3(6):527-532.
51. Amabile P G, Waugh J M, Lewis T N, Elkins C J, Janas W, Dake M D. High-Efficiency Endovascular Gene Delivery Via Therapeutic Ultrasound. Journal Of The American College Of Cardiology. 2001; 37(7):1975-1980.
52. Manome Y, Nakamura M, Ohno T, Furuhata H. Ultrasound Facilitates Transduction of Naked Plasmid DNA Into Colon Carcinoma Cells In Vitro And In Vivo. Human Gene Therapy. 2000; 11(11):1521-1528.
53. Barbarese E, Ho S-Y, D'arrigo J S, Simon R H. Internalization of Microbubbles by Tumor Cells In Vivo And In Vitro. Journal of Neuro-Oncology. 1995; 26:25-34.
54. Cho C-W, Liu Y, Cobb W N, et al. Ultrasound-Induced Mild Hyperthermia as A Novel Approach to Increase Drug Uptake In Brain Microvessel Endothelial Cells. Pharm Res. 2002; 19(8): 1123-1129.
55. Mesiwala Ah, Farrell L, Wenzel Hj, Et al. High-Intensity Focused Ultrasound Selectively Disrupts the Blood-Brain Barrier In Vivo, Ultrasound Med Biol. 2002; 28(3):389-400.
56. Cho Cw, Liu Y, Cobb W N, Et al. Ultrasound-Induced Mild Hyperthermia as A Novel Approach To Increase Drug Uptake In Brain Microvessel Endothelial Cells. Pharmaceutical Research. 2002; 19(8):1123-1129.
57. Hynynen K, Mcdannold N, Martin H, Jolesz Fa, Vykhodtseva N. The Threshold for Brain Damage In Rabbits Induced By Bursts Of Ultrasound In The Presence Of An Ultrasound Contrast Agent (Optison®). Ultrasound in Medicine and Biology. 2003; 29(3):473-481.
58. Guillaume C, Delepine P, Droal C, Montier T, Tymen G, Claude F, Aerosolization Of Cationic Lipid-DNA Complexes: Lipoplex Characterization And Optimization Of Aerosol Delivery Conditions. Biochem Biophys Res Commun. 2001; 286(3):464-471.
59. Pillai R, Petrak K, Bleziniger P, Et al. Ultrasonic Nebulization Of Cationic Lipid-Bused Gene Delivery Systems For Airway Administration. Pharm Res. 1998; 15(1):1743-1747.
60. Mitragotri S, Kost J. Low-Frequency Sonophoresis. A Review. Adv Drug Deliv Rev. 2004; 56:589-601.
61. Barry Bw, Novel Mechanisms and Devices to Enable Successful Transdermal Drug
Delivery. European Journal of Pharmaceutical Sciences, 2001; 14:101-114. Prausnitz M R. Reversible Skin Permeabilization for Transdermal Delivery of Macromolecules. Critical Reviews in
Therapeutic Drug Carrier Systems. 1997; 14(4):455-483.
62. Guy R H. Current Status And Future Prospects of Transdermal Drug Delivery. Pharm Res. 1996; 13(12): 1765-1769.
63. Kassan D G, Lynch Am, J Sm. Physical Enhancement of Dermatologic Drug Delivery—Iontophoresis And Phonophoresis. J Amer Acad Dermatology. 1996; 34(4):657-666.
64. Byl N N. The Use of Ultrasound as An Enhancer for Transcutaneous Drug Delivery: Phonophoresis. Physical Therapy. 1995; 75(6):539-553.
65. Tyle P, Agrawala P. Drug Delivery By Phonophoresis. Pharm Res. 1989; 6(5):355-361.
66. Skauen Dm, Zentner G M, Phonophoresis. Int J Pharmaceutics. 1984; 20:235-245.
67. Bommannan D, Okuyama H, Stauffer P, Guy R H. Sonophoresis. I the Use Of High-Frequency Ultrasound To Enhance Transdermal Drug Delivery. Pharm Res. 1992; 9(4):559-564.
68. Bommannan D, Menon G K, Okuyama H, Elias P M, Guy R H. Sonophoresis. IiExamination of the Mechanism (S) Of Ultrasound-Enhanced Transdermal Drug Delivery. Pharm Res. 1992; 9(8): 1043-1047.
69. Menon G K. Bommannan D B, Elias P M. High-Frequency Sonophoresis: Permeation Pathways and Structural Basis for Enhanced Permeability. Skin Pharmacol. 1994; 7: 130-139.
70. Vyas Sp, Singh R, Asati Rk. Liposomally Encapsulated Diclofenac for Sonophoresis Induced Systemic Delivery. J Microencapsul. 1995; 12(2):149-154.
71. Mitragotri S. Synergistic Effect of Enhancers for Transdermal Drug Delivery. Pharm Res. 2000; 17(11): 1354-1357.
72. Johnson M E, Mitragotri S, Patel A, Blankschtein D, Langer R. Synergistic Effects of Chemical Enhancers and Therapeutic Ultrasound on Transdermal Drug Delivery. Journal of Pharmaceutical Sciences. 1996; 85(7):670-677.
73. Tezel A, Sens A, Tuchscherer J, Mitragotri A. Synergistic Effect of Low-Frequency Ultrasound and Surfactants on Skin Permeability. J Pharm Sci. 2002; 91(1):91-100.
74. Wu J, Chappelow J, Yang J. Weimann L. Defects Generated In Human Stratum Corneum Specimens by Ultrasound, Ultrasound In Med & Biol. 1998; 24(5):705-710.
75. Yamashita N, Tachibana K, Ogawa K, Tsujita N, Tornita A. Scanning Electron Microscopic Evaluation of The Skin Surface After Ultrasound Exposure. Anatom Rec. 1997; 247:455-461.

76. Tezel A, Mitragotri S. On The Origin of Size-Dependent Tortuosity for Permeation of Hydrophilic Solutes Across the Stratum Corneum. Journal Of Controlled Release. 2003; 86(1): 183-186.
77. Tezel A. Sens A. Mitragotri S. Description of Transdermal Transport of Hydrophilic Solutes During Low-Frequency Sonophoresis Based on A Modified Porous Pathway Model. 2003; 92(2):381-393.
78. Kwok C S, Mourad P D, Crum L A, Ratner B D. Self-Assembled Molecular Structures As Ultrasonically-Responsive Barrier Membranes for Pulsatile Drug Delivery. J Biomed Mater Res. 2001; 57: 151-164.
79. Francis C W, Onundarson P T, Carstensen E, et al. Enhancement of Fibrinolysis In Vitro By Ultrasound. J Clin Invest. 1992; 90(11):2063-2068.
80. Lauer C G, Burge R, Tang D R, Bass B G, Gomez Er, Alving Bm. Effect of Ultrasound On Tissue-Type Plasminogen Activator-Induced Thrombolysis. Circulation. 1992; 86:1257-1264.
81. Wu Y Q, Unger E C, Mccreery T P, et al. Binding And Lysing of Blood Clots Using Mrx-408. Investigative Radiology. 1998; 33(12):880-885.
82. Culp W C, Porter T R, Lowery J, Roberson P K, Xie F, Mccowan T C. Intracranial Clot Lysis With Intravenous Platelet Targeted Microbubbles And Transcranial Ultrasound. Circulation. 2003; 108(17):604-604.
83. Kost J. Ultrasound for Controlled Delivery of Therapeutics. Clinical Materials. 1993; 13:155-161.
84. Loverock P, Ter Haarg, Ormerod M G, Imrie P R. The Effect of Ultrasound on the Cytoxicity of Adriamycin. Brit J Radiol. 1990; 63:542-546.
85. McCulloch, M., C. Gresser, S. Moos, J. Odabashian, S, Jasper, J. Bednarz, P. Burgess, D. Carney, V. Moore, E. Sisk, A. Waggoner, S. Witt, and D. Adams. Ultrasound contrast physics: A series on contrast echocardiography. J Am Soc Echocardiogr. 13:10, pp. 959-67, 2000.
86. Harisinghani, Mukesh G.; Weissleder, Ralph; Schima, Wolfgang; Saini, Sanjay; Hahn, Peter F.; Mueller, Peter R. (2001), MRI Contrast Agents for Evaluating Focal Hepatic Lesions, 56, Clinical Radiology, pp. 714-725).
87. Contrast Agents II: Optical, Ultrasound, X-Ray Imaging and Radiopharmaceutical Imaging (Topics in Current Chemistry, Werner Krause (Editor), 2010, Springer

What is claimed is:

1. A system of ultrasonic delivery of at least one of a drug, drug carrier, and imaging contrast agent, comprising:
an acoustic power source coupled to an acoustic transducer;
wherein said acoustic transducer is configured to be placed upon a patient's delivery zone for the at least one of drug, drug carrier, and imaging contrast agent, further wherein said acoustic transducer is configured to transmit an acoustic field to said patient's delivery zone;
a probe is configured to be placed over or within the patient's delivery zone;
wherein the at least one drug, drug carrier, and imaging contrast agent comprises a ligand structured to selectively form a catch bond or a slip bond with a receptor in said patient's delivery zone;
a control computer configured to control the acoustic power source and programmed to selectively form said catch bond or said slip bond by modifying the acoustic field via the acoustic transducer;
wherein the control computer is configured to: (i) receive inputs comprising patient and drug parameters, (ii) calculate a sonification program based on the patient and drug parameters, the sonification program configured to modify the acoustic field, and (iii) execute the sonification program; and
further wherein the control computer is configured to receive data from the probe.

2. The ultrasonic delivery system of claim 1, wherein:
said control computer is coupled to a network for one or more of remote observation and remote control of said ultrasonic delivery system.

3. The ultrasonic delivery system of claim 1, wherein said acoustic power source has an operating frequency of 0.1 MHz-20 MHz.

4. The ultrasonic delivery system of claim 1, wherein the system is configured to have an application duration for a particular period of time wherein the particular period of time is from one second to ten hours.

5. The ultrasonic delivery system of claim 1, wherein said acoustic transducer is a focusing ultrasonic transducer.

6. The ultrasonic delivery system of claim 1, wherein said sonification program is configured to modify a depth, an intensity, and a duty cycle.

* * * * *